United States Patent [19]
Furuya et al.

[11] Patent Number: 6,001,850
[45] Date of Patent: Dec. 14, 1999

[54] THIENOPYRIDINE DERIVATIVES, THEIR PRODUCTION AND USE

[75] Inventors: Shuichi Furuya; Hirokazu Matsumoto; Yoji Hayase; Nobuhiro Suzuki; Takashi Imada, all of Tsukuba, Japan

[73] Assignee: Takeda Chemical Industries, Ltd., Osaka, Japan

[21] Appl. No.: 08/894,318

[22] PCT Filed: Apr. 24, 1997

[86] PCT No.: PCT/JP97/01434

§ 371 Date: Aug. 14, 1997

§ 102(e) Date: Aug. 14, 1997

[87] PCT Pub. No.: WO97/41126

PCT Pub. Date: Nov. 6, 1997

[30] Foreign Application Priority Data

Apr. 26, 1996 [JP] Japan ................................. 8-107650
Apr. 30, 1996 [JP] Japan ................................. 8-109788
Apr. 30, 1996 [JP] Japan ................................. 8-109789

[51] Int. Cl.$^6$ ........................ A61K 31/435; C07D 495/04
[52] U.S. Cl. ............................................ 514/301; 546/114
[58] Field of Search ............................ 546/114; 514/301

[56] References Cited

U.S. PATENT DOCUMENTS 5,817,819  10/1998  Furuya et al. .......................... 546/314

FOREIGN PATENT DOCUMENTS 0 443 568 A1   8/1991   European Pat. Off. .
0 520 423 A2  12/1992   European Pat. Off. .
94/20460       9/1994   WIPO .
95/28405      10/1995   WIPO .

OTHER PUBLICATIONS

P. Gilis et al., "Synthesis and antibacterial evaluation of 4,7–dihydro–4–oxothienol[2,3–b]pyridine–5–carboxylic acids", European Journal of Medicinal Chemistry, Chimica Therapeutica, May–Jun., 1978–13, No. 3, pp. 265–269.

*Primary Examiner*—Bernard Dentz
*Attorney, Agent, or Firm*—Wenderoth, Lind & Ponack, L.L.P.

[57] ABSTRACT

The present thienopyridine derivatives and composition having gonadotropin-releasing hormone antagonistic activity are useful as prophylactic or therapeutic agents for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agent in both sexes (e.g. a pregnancy controlling agent and a menstrual cycle controlling agent); is useful as a contraceptive of male or female, as an ovulation-inducing agent of female; is useful as an infertility treating agent by using a rebound effect owing to a stoppage of administration thereof; is useful as modulating estrous cycles in animals in the field of animal husbandry, as an agent for improving the quality of edible meat or promoting the growth of animals; is useful as an agent of spawning promotion in fish.

14 Claims, No Drawings

THIENOPYRIDINE DERIVATIVES, THEIR PRODUCTION AND USE

This application is a 371 of PCT/JP97/01434 filed Apr. 24, 1997.

TECHNICAL FIELD

The present invention relates to novel 4,7-dihydro-4-oxothieno[2,3-b]pyridine derivatives and salts thereof. The present invention further relates to method for manufacturing these 4,7-dihydro-4-oxothieno[2,3-b]pyridine derivatives and salts thereof, and pharmaceutical composition containing these 4,7-dihydro-4-oxothieno[2,3-b]pyridine derivatives and salts thereof.

BACKGROUND ART

Secretion of anterior pituitary hormone undergoes the control by peripheral hormone secreted from target organs for the respective hormones and by secretion-accelerating or secretion-inhibiting hormone from hypothalamus, which is the upper central organ of anterior lobe of pituitary (in this specification, these hormones are collectively called "hypothalamic hormone"). At the present stage, as hypothalamic hormones, nine kinds of hormones including, for example, thyrotropin releasing hormone (TRH) or gonadotropin releasing hormone {GnRH: sometimes called as LH-RH (luteinizing hormone releasing hormone)} are confirmed their existence. These hypothalamic hormones are assumed to show their actions via the receptor which is considered to exist in the anterior lobe of pituitary, and observational studies of receptor genes specific to these hormones, including cases of human, have been developed. Accordingly, antagonists or agonists specifically and selectively control the action of hypothalamic hormone by acting on these receptors and control the secretion of anterior pituitary hormone. As the results, they are expected to be useful for prophylactic and therapeutic agents of anterior pituitary hormone dependent diseases.

As compounds having such GnRH antagonistic activity, a number of compounds including, for example, derivatives of GnRH such as straight-chain peptides (U.S. Pat. No. 5,140,009, U.S. Pat. No. 5,171,835), cyclic hexapeptide derivatives (Japanese Patent Application Laid-open No.S61 (1986)-191698) or bicyclic peptide derivatives (Journal of Medicinal Chemistry, Vol.36, pp.3265–3273, 1993). Furthermore, as non-peptide compounds having such GnRH antagonistic activity, compounds described in PCT International Publication No. WO 95/28405 are known.

Such peptide compounds leave many problems including, for example, oral administrability, dosage form, stability of the drug, durability of actions, stability on metabolism. It has been desired to obtain GnRH antagonists which have excellent characteristics of high GnRH antagonistic activity, oral administrability, stability in plasma of blood and durability of actions.

The object of the invention lies in providing novel 4,7-dihydro-4-oxothieno[2,3-b]pyridine derivatives having excellent gonadotropin releasing hormone antagonistic activity.

DISCLOSURE OF INVENTION

The present invention provides 4,7-dihydro-4-oxo-thieno [2,3-b]pyridine derivatives having excellent properties of high GnRH antagonistic activity, oral administrability, stability in plasma in blood, and durability of actions.

The present invention is directed to:
1. A compound represented by the formula (I):

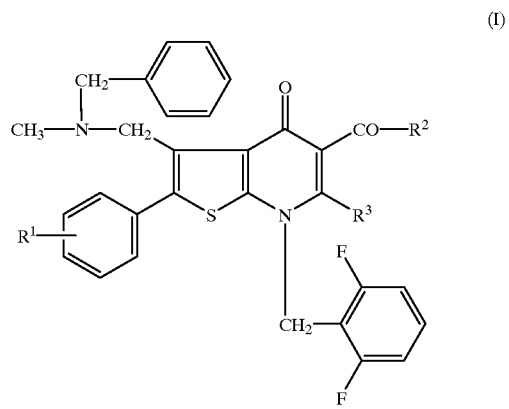

wherein (A)$R^1$ is (1)an alkoxy group which is substituted with a group selected from the group consisting of (i)halogen, (ii)cycloalkyl and (iii)alkenyl, $R^2$ is (1)an alkyl group, (2)an aryl group, (3)a group of the formula: —X—$R^{41}$, wherein $R^{41}$ is an optionally substituted alkyl group or an optionally substituted cycloalkyl group and X is O or S, and $R^3$ is a hydrogen atom or an alkyl group; or (B)$R^1$ is a $C_{1-8}$ alkanoylamino group, $R^2$ is (1)a group of the formula: —X—$R^{43}$, wherein when X is O, $R^{43}$ is an optionally substituted branched alkyl group, an optionally substituted cycloalkyl group or an optionally substituted 6-membered oxygen-containing heterocyclic group, and when X is S, $R^{43}$ is an optionally substituted alkyl group, an optionally substituted cycloalkyl group or an optionally substituted 6-membered oxygen-containing heterocyclic group or (2)a hydroxyl group, and $R^3$ is a hydrogen atom or an alkyl group, or a salt thereof.

2. A compound according to the item 1, wherein $R^1$ is a $C_{1-6}$ alkoxy group which is substituted with a group selected from the group consisting of (i)halogen, (ii)$C_{3-10}$ cycloalkyl and (iii)$C_{2-9}$ alkenyl, $R^2$ is a group of the formula: —X—$R^{42}$, wherein $R^{42}$ is an optionally substituted $C_{1-13}$ alkyl group or an optionally substituted $C_{3-10}$ cycloalkyl group, and X is O or S, and $R^3$ is a hydrogen atom or an $C_{1-6}$ alkyl group.

3. A compound according to the item 2, wherein $R^{42}$ is (1)$C_{1-13}$ alkyl which may optionally be substituted with halogen, $C_{1-4}$ alkoxy or $C_{3-8}$ cycloalkyl or (2)$C_{3-10}$ cycloalkyl which may optionally be substituted with halogen, $C_{1-4}$ alkoxy or $C_{1-4}$ alkyl.

4. A compound according to the item 2, wherein $R^1$ is a $C_{1-3}$ alkoxy group which is substituted with vinyl.

5. A compound according to the item 2, wherein $R^1$ is allyloxy.

6. A compound according to the item 2, wherein $R^2$ is (1)$C_{1-3}$ alkyl group, (2)$C_{6-14}$ aryl group or (3)$C_{5-7}$ alkoxy group which may optionally be substituted with halogen, $C_{1-3}$ alkyl or $C_{1-3}$ alkoxy.

7. A compound according to the item 2, wherein $R^2$ is isopropyl, phenyl or isopropoxy.

8. A compound according to the item 1, wherein $R^1$ is a $C_{1-8}$ alkanoylamino group, $R^2$ is (1)a group of the formula: —X—$R^{44}$, wherein when X is O, $R^{44}$ is an optionally substituted $C_{3-13}$ branched alkyl group, an optionally substituted $C_{3-10}$ cycloalkyl group or an optionally substituted 6-membered oxygen-containing heterocyclic group, and when X is S, $R^{44}$ is an optionally substituted $C_{1-13}$ alkyl group, an optionally substituted $C_{3-10}$ cycloalkyl group or an optionally substituted 6-membered oxygen-containing heterocyclic group, or (2)a hydroxyl group, and $R^3$ is a hydrogen atom or a $C_{1-6}$ alkyl group.

9. A compound according to the item 8, wherein (1) when X is O, $R^{44}$ is a $C_{3-13}$ branched alkyl group which may optionally be substituted with $C_{1-4}$ alkyl, halogen, amino, mono- or di-$C_{1-4}$ alkylamino, $C_{1-4}$ alkoxy or $C_{3-7}$ cycloalkyl; a $C_{3-10}$ cycloalkyl group which may optionally be substituted with halogen, nitro, $C_{1-4}$ alkyl, $C_{1-4}$ alkoxy, amino, mono- or di-$C_{1-4}$ alkylamino; or a 6-membered oxygen-containing heterocyclic group which may optionally be substituted with halogen, nitro, oxo, hydroxy, amino, mono- or di-$C_{1-4}$ alkylamino, $C_{1-4}$ alkoxy, $C_{1-4}$ alkyl or $C_{1-4}$ alkylthio; or (2) when X is S, $R^{44}$ is a $C_{1-13}$ alkyl group which may optionally be substituted with halogen, amino, mono- or di-$C_{1-4}$ alkylamino, $C_{1-4}$ alkoxy or $C_{3-7}$ cycloalkyl; or a 6-membered oxygen-containing heterocyclic group which may optionally be substituted with halogen, nitro, oxo, hydroxy, amino, mono- or di-$C_{1-4}$ alkylamino, $C_{1-4}$ alkoxy, $C_{1-4}$ alkyl or $C_{1-4}$ alkylthio.

10. A compound according to the item 8, wherein $R^1$ is a $C_{3-5}$ alkanoylamino group.

11. A compound according to the item 8, wherein $R^1$ is isobutyrylamino.

12. A compound according to the item 8, wherein X is O, and $R^{44}$ is an optionally substituted $C_{3-7}$ branched alkyl group or an optionally substituted 6-membered oxygen-containing heterocyclic group.

13. A compound according to the item 8, wherein X is S and $R^{44}$ is an optionally substituted alkyl group, or a 6-membered oxygen-containing heterocyclic group which may optionally be substituted.

14. A compound according to the item 1, which is 2-(4-allyloxyphenyl)-4,7-dihydro-7-(2,6-difluorobenzyl)-3-(N-benzyl-N-methylaminomethyl)-5-isobutyryl-4-oxothieno[2,3-b]pyridine; 2-[4-(2-methyl-2-propen-1-yloxy)phenyl]-4,7-dihydro-7-(2,6-difluorobenzyl)-3-(N-benzyl-N-methylaminomethyl)-5-isobutyryl-4-oxothieno[2,3-b]pyridine; isopropyl [2-(4-allyloxyphenyl)-4,7-dihydro-7-(2,6-difluorobenzyl)-3-(N-benzyl-N-methylaminomethyl)-6-methyl-4-oxothieno[2,3-b]pyridine-5-carboxylate]; ethyl (2-(4-allyloxyphenyl)-4,7-dihydro-7-(2,6-difluorobenzyl)-3-(N-benzyl-N-methylaminomethyl)-6-methyl-4-oxothieno[2,3-b]pyridine-5-carboxylate), or a salt thereof.

15. A compound according to the item 1, which is isopropyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; sec-butyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; cyclohexyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; 3-pentyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; tetrahydropyranyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; 4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylic acid; 2,4-dimethyl-3-pentyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; isopropyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate]; cyclohexyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate]; 3-pentyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate]; 4-tetrahydropyranyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate], or a salt thereof.

16. A compound according to the item 1, which is 4,7-dihydro-7-(2,6-difluorobenzyl)-3-(N-benzyl-N-methylaminomethyl)-2-(4-isobutyrylaminophenyl)-4-oxo-5-(4-tetrahydropyranyl-thiocarbonyl)thieno[2,3-b]pyridine, or its salt.

17. Ethyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate] or its salt.

18. Ethyl [4,7-dihydro-7-(2,6-difluorobenzyl)-3-(N-benzyl-N-methylaminomethyl)-2-(4-isobutyrylaminophenyl)-6-ethyl-4-oxothieno[2,3-b]pyridine-5-carboxylate] or its salt.

19. A method for producing a compound of the formula (I) or a salt thereof, which comprises (a) reacting a compound of the formula (II):

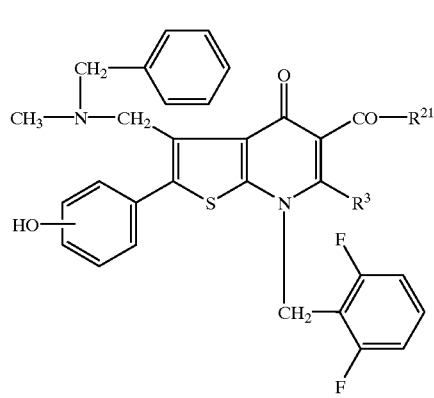

(II)

wherein $R^{21}$ is (1)an alkyl group, (2)an aryl group, (3) a group of the formula: —X—$R^{41}$, wherein $R^{41}$ is an optionally substituted alkyl group or an optionally substituted cycloalkyl group and —X— is O or S, or its salt, with a compound of the formula:

$R^{12}$—Y wherein $R^{12}$ is an alkyl group which is substituted with a group selected from the group consisting of (i)halogen, (ii)cycloalkyl and (iii)alkenyl, and Y is a halogen atom, to produce a compound of the formula (III):

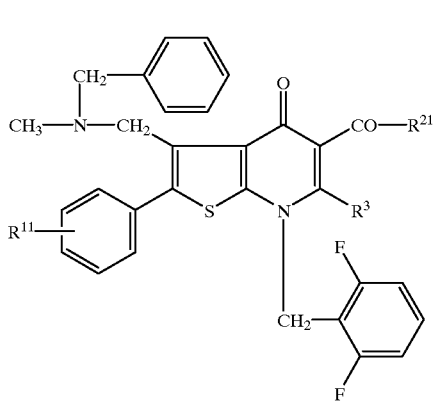

(III)

wherein $R^{11}$ is an alkoxy group which is substituted with a group selected from the group consisting of (i)halogen, (ii)cycloalkyl and (iii)alkenyl, and $R^3$ is a hydrogen atom or an alkyl group, or a salt thereof, (b) reacting a compound of the formula (IV):

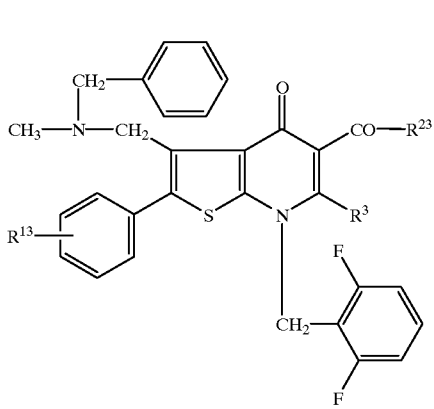

(IV)

wherein $R^{13}$ is a $C_{1-8}$ alkanoylamino group, $R^{23}$ is a straight-chain alkoxy group, and $R^3$ is a hydrogen atom or an alkyl group, with a compound of the formula:

$R^{24}$—OH wherein $R^{24}$ is an optionally substituted branched alkyl group, an optionally substituted cycloalkyl group or an optionally substituted 6-membered oxygen-containing heterocyclic group, or with a compound of the formula:

$R^{25}$—SH wherein $R^{25}$ is an optionally substituted alkyl group, an optionally substituted cycloalkyl group or an optionally substituted 6-membered oxygen-containing heterocyclic group, or alternatively subjecting the compound (IV) to hydrolysis, to produce a compound of the formula (V):

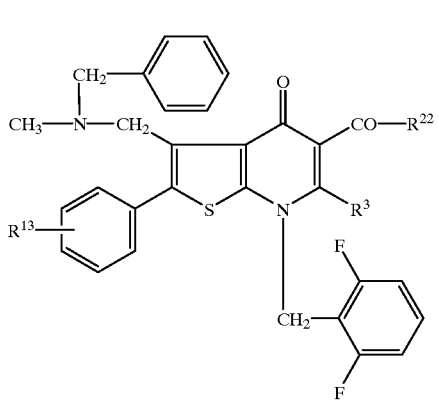

(V)

whereion $R^{13}$ has the same meaning as defined above, $R^{22}$ is (1) a group of the formula: —X—$R^{43}$, wherein when X is O, $R^{43}$ is an optionally substituted branched alkyl group, an optionally substituted cycloalkyl or an optionally substituted 6-membered oxygen-containing heterocyclic group, and when X is S, $R^{43}$ is an optionally substituted alkyl group, an optionally substituted cycloalkyl group or an optionally substituted 6-membered oxygen-containing heterocyclic group or (2) a hydroxyl group, or a salt thereof, or (c) reacting a compound of the formula (VI):

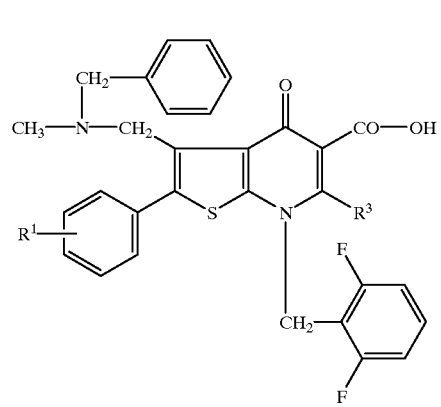

(VI)

wherein $R^1$ is (1) an alkoxy group which is substituted with a group selected from the group consisting of (i)halogen, (ii)cycloalkyl and (iii)alkenyl, or (2) $C_{1-8}$ alkanoylamino group, and $R^3$ is a hydrogen atom or an alkyl group, with a compound of the formula:

$R^{27}$—H wherein $R^{27}$ is a group of the formula: —X—$R^4$, whererin $R^4$ is an optionally substituted alkyl group, an optionally substituted cycloalkyl group or an optionally substituted 6-membered oxygen-containing heterocyclic group and X is O or S, to produce a compound of the formula (VII):

(VII)

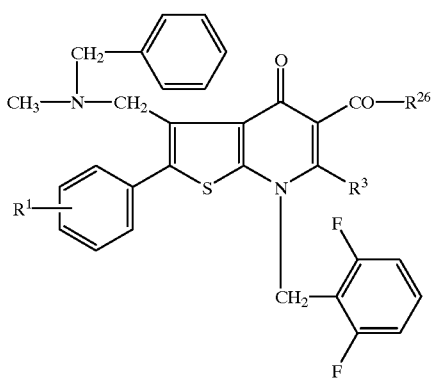

wherein (A)R$^1$ is (1)an alkoxy group which is substituted with a group selected from the group consisting of (i)halogen, (ii) cycloalkyl and (iii) alkenyl, R$^{26}$ is (1) an alkyl group, (2)an aryl group, (3)a group of the formula: —X—R$^{41}$, wherein R$^{41}$ is an optionally substituted alkyl group or an optionally substituted cycloalkyl group and X is O or S, and R$^3$ is a hydrogen atom or an alkyl group; or (B)R$^1$ is a C$_{1-8}$ alkanoylamino group, R$^{26}$ is (1)a group of the formula: —X—R$^{43}$, wherein when X is O, R$^{43}$ is an optionally substituted branched alkyl group, an optionally substituted cycloalkyl group or an optionally substituted 6-membered oxygen-containing heterocyclic group and when X is S, R$^{43}$ is an optionally substituted branched alkyl group, an optionally substituted cycloalkyl group or an optionally substituted 6-member ed oxygen-containing heterocyclic group, and R$^3$ is a hydrogen atom or an alkyl group.

20. A method for producing a compound of the formula (IX):

(IX)

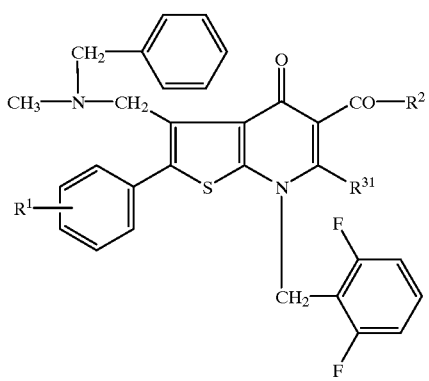

wherein (A)R$^1$ is (1)an alkoxy group which is substituted with a group selected from the group consisting of (i)halogen, (ii)cycloalkyl and (iii)alkenyl, R$^2$ is (1)an alkyl group, (2)an aryl group, (3)a group of the formula: —X—R$^{41}$, wherein R$^{41}$ is an optionally substituted alkyl group or an optionally substituted cycloalkyl group and X is O or S, and R$^3$ is a hydrogen atom or an alkyl group; or (B)R$^1$ is a C$_{1-8}$ alkanoylamino group, R$^2$ is (1)a group of the formula: —X—R$^{45}$, wherein when X is O, R$^{45}$ is an optionally substituted branched alkyl group, an optionally substituted cycloalkyl group or an optionally substituted 6-membered oxygen-containing heterocyclic group, and when X is S, R$^{45}$ is an optionally substituted alkyl group, an optionally substituted cycloalkyl group or an optionally substituted 6-membered oxygen-containing heterocyclic group, and R$^3$ is a hydrogen atom or alkyl group, or a salt thereof, which comprises reacting a compound of the formula (VIII):

(VIII)

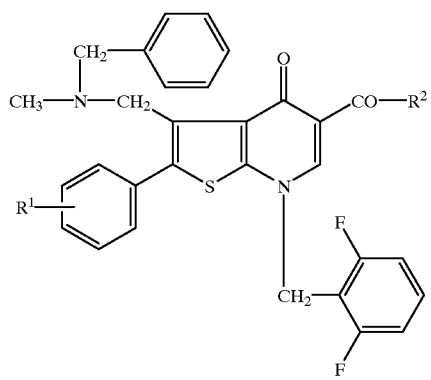

wherein R$^1$ and R$^2$ have the same meanings as defined above with a compound of the formula:

R$^{32}$—Z wherein R$^{32}$ is an alkyl group and Z is a metal optionally be halogenated, or its salt.

21. A compound according to the item 1, which has a chracteristic of high bioavailability when orally administered.

22. A compound according to the item 1, which is stable in plasma of blood.

23. A pharmaceutical composition, which comprises a compound as defined in the item 1 and a carrier, excipient or diluent therefor.

24. A pharmaceutical composition according to the item 23, which is a composition for treating or preventing a sex hormone dependent disease.

25. A pharmaceutical composition according to the item 24, wherein the sex hormone dependent disease is prostatic cancer, uterus cancer, breast cancer or pituitary adenoma.

26. A pharmaceutical composition according to the item 25, wherein the sex hormone dependent disease is prostatauxe, endometriosis, myoma uteri or precocious puberty.

27. A pregnancy controlling composition, which comprises a compound or a salt thereof as defined in the item 1 and a carrier, excipient or diluent therefor.

28. A menstrual cycle controlling composition, which comprises a compound or a salt thereof as defined in the item 1 and a carrier, excipient or diluent therefor.

29. A composition according to the item 27, which is a composition for contraception.

30. A method for treating a mammal suffering from a gonadotropin-releasing hormone derived disorder, which comprises administering an effective amount of a compound as defined in the item 1 to the mammal.

31. Use of a compound as defined in the item 1 for producing a pharmaceutical composition for antagonizing gonadotropin-releasing hormone activity in a mammal suffering from a sex hormone dependent disease.

The nucleus of the present compound, 4,7-dihydro-4-oxo-thieno[2,3-b]pyridine, is shown in the following formula (X):

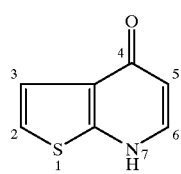

(X)

As the alkoxy group in the "alkoxy group substituted with a group selected from (i)halogen, (ii)cycloalkyl and (iii) alkenyl" in $R^1$ of the above formulae, an $C_{1-6}$ alkoxy group is preferable. The examples of the $C_{1-6}$ alkoxy group are exemplified by methoxy, ethoxy, propoxy, isopropoxy, n-butoxy, isobutoxy, sec-butoxy, tert-butoxy, pentoxy and hexyloxy. Among others, $C_{1-4}$ alkoxy group or $C_{1-3}$ alkoxy group is preferable, and methoxy is especially preferable.

As the examples of the halogen, which is a substituent on the alkoxy group, mention is made of fluorine, chlorine, bromine and iodine. Among them, fluorine is preferable.

As the cycloalkyl group, which is a substituent on the alkoxy group, $C_{3-10}$ cycloalkyl group is preferable, and which is exemplified by cyclopropyl, cyclobutyl, cyclopentyl, cyclohexyl, cycloheptyl, cyclooctyl and cyclononyl. Among them, $C_{3-6}$ cycloalkyl is preferable, and cyclopropyl is especially preferable.

As the alkenyl group, which is a substituent on the alkoxy group, $C_{2-10}$ alkenyl group is preferable, and which is exemplified by vinyl, allyl, 1-butenyl, 2-butenyl, butadienyl, isopropenyl, hexatrienyl and 3-octenyl. Among them, $C_{2-6}$ alkenyl group is preferable, and $C_{2-4}$ alkenyl group is more preferable.

The alkenyl group may have an alkyl group as a substituent, and the alkenyl group which has an alkyl group as a substituent is also called as "alkenyl group". As the alkyl, $C_{1-6}$ alkyl is preferable, and which is exemplified by methyl, ethyl, n-propyl, isopropyl, n-butyl, isobutyl, sec-butyl, tert-butyl, pentyl and hexyl. Among them, $C_{1-4}$ alkyl is more preferable, $C_{1-3}$ alkyl is still more preferable, and methyl is especially preferable.

Examples of the "alkenyl group substituted with alkyl" include $C_{2-13}$ alkenyl group, preferably $C_{2-9}$ alkenyl group, preferably $C_{2-7}$ alkenyl group.

Preferable examples of the "alkenyl group substituted with alkyl" include 2-methyl-allyl.

The number of substituents in $R^1$ is preferably 1 to 3, especially 1 to 2.

In the compound (I), as preferable examples of the group $R^1$, mention is made of (1)$C_{1-6}$ alkoxy group which is substituted with a group selected from the group consisting of (i)halogen, (ii)$C_{3-10}$ cycloalkyl and (iii)$C_{2-10}$ alkenyl; (2)$C_{1-6}$ alkoxy group which is substituted with a group selected from the group consisting of (i)halogen, (ii)$C_{3-10}$ cycloalkyl and (iii)$C_{2-6}$ alkenyl; (3)$C_{2-6}$ alkoxy group which is substituted with a group selected from the group consisting of (i)halogen, (ii)$C_{3-6}$ cycloalkyl and (iii)$C_{2-6}$ alkenyl; (4)$C_{1-4}$ alkoxy group which is substituted with $C_{2-6}$ alkenyl. As especially preferable examples, mention is made of (5)vinyl-$C_{1-3}$ alkoxy group and allyloxy.

As the alkyl group shown by $R^2$, $C_{1-6}$ alkyl group is preferable, and is exemplified by methyl, ethyl, n-propyl, isopropyl, butyl, isobutyl, sec-butyl, tert-butyl, pentyl and hexyl. Among them, $C_{1-4}$ alkyl group is preferable and $C_{1-3}$ alkyl group is more preferable. Furthermore, $C_3$ alkyl group (n-propyl, isopropyl) is especially preferable.

As the aryl group shown by $R^2$, $C_{6-14}$ aryl group is preferable, and which is exemplified by phenyl, naphthyl, anthryl, phenanthryl, acenaphthyl and anthracenyl. Among them, phenyl and naphthyl are preferable.

As the alkyl group of the optionally substituted alkyl group of $R^{41}$ in —X—$R^{41}$, wherein X is O or S, $R^{41}$ includes $C_{1-13}$ alkyl group is preferable and which includes straight-chain or branched alkyl group. The straight-chain alkyl group includes methyl, ethyl, n-propyl, n-butyl, n-pentyl, n-hexyl and n-octyl. The branched alkyl includes isopropyl, isobuthyl, sec-buthyl, tert-buthyl, isopentyl, sec-pentyl, tert-pentyl, 3-pentyl, neopentyl, isohexyl, sec-hexyl, tert-hexyl, iso-octyl, sec-octyl and tert-octyl. Preferable examples of the alkyl group include $C_{1-9}$ alkyl group, $C_{1-7}$ alkyl group and $C_{1-6}$ alkyl group. Preferble examples of the branched alkyl group include branched $C_{3-13}$ alkyl group, branched $C_{3-9}$ alkyl group, branched $C_{3-8}$ alkyl group, branched $C_{3-7}$ alkyl group and branched $C_{3-6}$ alkyl group.

As the alkoxy group represented by the group —X—$R^{41}$, in which X is O and $R^{41}$ is the optionally substituted alkyl, $C_{1-13}$ alkoxy group is preferable, and the examples of the alkoxy group include methoxy, ethoxy, propoxy, isopropoxy, butoxy, isobutoxy, sec-butoxy, tert-butoxy, pentyloxy, isopentyloxy, sec-pentyloxy, tert-pentyloxy, 3-pentyloxy, neopentyloxy, hexyloxy, isohexyloxy, sec-hexyloxy, tert-hexyloxy, octyloxy, isooctyloxy, sec-octyloxy, tert-octyloxy. As preferable examples of the alkoxy group, mention is made of $C_{1-10}$ alkoxy group, $C_{1-9}$ alkoxy group, $C_{1-8}$ alkoxy group, $C_{1-7}$ alkoxy group. Among others, $C_{3-9}$ alkoxy group, $C_{3-8}$ alkoxy group, $C_{3-7}$ alkoxy group and $C_3$ alkoxy group (i.e. n-propoxy, isopropoxy) are more preferable.

As the substituents on the alkyl group in the optionally substituted alkyl group (which includes the optionally substituted branched alkyl group) shown by $R^{41}$ in —X—$R^{41}$ of $R^2$ and the substituents on the cycloalkyl group in the optionally substituted cycloalkyl group of $R^{41}$ in the group —X—$R^{41}$ of $R^2$, mention is made of (1)halogen, (2)alkoxy, (3)alkyl, (4)cycloalkyl, (5)alkylthio, (6)amino, (7)mono- or di-$C_{1-4}$ alkylamino, (8)nitro, (9)hydroxyl, (10)oxo, (11) carbamoyl, (12)cyano, (13)mercapto and (14)sulfo.

The number of the substituents is preferably 1 to 6, more preferably 1 to 3 and still more preferably 1 or 2. As more preferable examples of the substituents include halogen, nitro and amino.

As the alkoxy group represented by the group —X—$R^{41}$ wherein X is O and $R^{41}$ is an optionally substituted alkyl group, it includes 2-indanyloxy, 4-piperidinyloxy, tetrahydro-4H-pyra-4-nyloxy.

The halogen is exemplified by fluorine, chlorine, bromine and iodine. Among them, fluorine and chlorine are preferable.

As the alkoxy, $C_{1-4}$ alkoxy is preferable, and is exemplified by methoxy, ethoxy, propoxy, isopropoxy, butoxy, isobutoxy, sec-butoxy and tert-butoxy. Among others, methoxy is especially preferable.

As the alkyl, $C_{1-4}$ alkyl is preferable, and is exemplified by methyl, ethyl, n-propyl, isopropyl, n-butyl, isobutyl, sec-butyl and tert-butyl. Among them, methyi and ethyl are especially preferable.

As the cycloalkyl, $C_{3-8}$ cycloalkyl is preferable, and is exemplified by cyclopropyl, cyclobutyl, cyclopentyl, cyclohexyl, cycloheptyl and cyclooctyl. Among others, $C_{3-7}$ cycloalkyl is preferable.

As the mono-alkylamino, mono-$C_{1-4}$ alkylamino is preferable. Examples of the mono-$C_{1-4}$ alkylamino include N-methyamino, N-ethylamino, N-propylamino, N-n-butylamino and N-isobutylamino. As the di-alkylamino, di-$C_{1-4}$ alkylamino is preferable. The di-$C_{1-4}$ alkylamino includes N,N-dimethyamino, N,N-diethylamino and N,N-dipropylamino.

As the alkylthio, $C_{1-4}$ alkylthio is preferable. Examples of the $C_{1-4}$ alkylthio includes methylthio, ethylthio, n-propylthio, isopropylthio, n-butylthio and isobutylthio.

As the substituents on the alkyl or cycloalkyl, $C_{1-4}$ alkyl is preferable.

The number of the substituents on the alkoxy group is 1 to 3, more preferable 1 or 2.

As the cycloalkyl group shown by $R^{41}$ in the group —X—$R^{41}$ of $R^2$, $C_{3-10}$ cycloalkyl group is preferable. Examples of the $C_{3-10}$ cycloalkyl group include cyclopropyl, cyclobutyl, cyclopentyl, cyclohexyl, cycloheptyl and cyclooctyl. Among others, $C_{3-8}$ cycloalkyl group and $C_{3-7}$ cycloalkyl group are preferable. The cycloalkyl group may form a bicyclic condensed ring group. Examples of the bicyclic condensed ring group includes indanyl. As the substituents on the cycloalkyl group, mention is made of the same group as those substituted on the alkyl group as described in the above.

Preferable substituents in the optionally substituted $C_{1-13}$ alkyl group of $R^{41}$ include halogen, $C_{1-4}$ alkoxy or $C_{3-8}$ cycloalkyl. Preferable substituents in the optionally substituted $C_{3-10}$ cycloalkyl group of $R^{41}$ include halogen, $C_{1-4}$ alkoxy or $C_{1-4}$ alkyl.

Preferable examples of the group $R^2$ include (A)(1) $C_{1-6}$ alkyl group, (2) $C_{6-14}$ aryl group or (3) a group of the formula: —X—$R^{42}$, wherein $R^{42}$ is an optionally substituted $C_{1-13}$ alkyl group or an optionally substituted $C_{3-10}$ cycloalkyl group, and X is O or S; (B)(1) $C_{1-6}$ alkyl group, (2) $C_{6-14}$ aryl group or (3) a group of the formula: —X—$R^{42}$, wherein $R^{42}$ is an optionally substituted $C_{1-9}$ alkyl group or an optionally substituted $C_{3-8}$ cycloalkyl group and X is O or S; (C)(1)$C_{1-6}$ alkyl group, (2)$C_{6-14}$ aryl group, (3)$C_{1-9}$ alkoxy group which may optionally be substituted with $C_{1-4}$ alkyl and (D) $C_{1-6}$ alkoxy group.

As the group $R^2$, (1)an $C_{1-3}$ alkyl group, (2)$C_{6-14}$ aryl group, (3)$C_{3-7}$ alkoxy group which may optionally be substituted with halogen, $C_{1-3}$ alkyl or $C_{1-3}$ alkoxy.

As the group $R^2$, isopropyl, phenyl, ethoxy, isopropoxy, sec-butoxy, 3-pentyloxy, 2,4-dimethyl-3-pentyloxy, ethylthio and isopropylthio are more preferable. Furthermore, as the group $R^2$, isopropyl, phenyl, isopropoxy, sec-butoxy, 3-pentyloxy, 2,4-dimethyl-3-pentyloxy are still more preferable.

The number of the substituents in the group $R^2$ is 1 to 3, more preferably 1 or 2.

As the alkyl group in $R^3$, $C_{1-6}$ alkyl group is preferable, and the examples of it is the same as those mentioned above. In particular, $C_{1-4}$ alkyl and $C_{1-3}$ alkyl are more preferable, and methyl and ethyl are still more preferable.

In the above formulae, examples of the $C_{1-8}$ alkanoylamino group shown by $R^1$ include formylamino, acetylamino, propionylamino, butyrylamino, isobutyrylamino, valerylamino, isovalerylamino, pivaloylamino, hexanoylamino, heptanoylamino and octanoylamino. As the alkanoylamino group shown by $R^1$, $C_{3-5}$ alkanoylamino is preferable, and isobutyrylamino is especially preferable.

The number of substituents of $R^1$ on the phenyl group at 2-position is one to two, especially one.

As preferable examples of the alkanlylamino group, $C_{3-5}$ alkanlylamino grooup is mentioned. Further, $C_{3-4}$ alkanlylamino group is more preferable, and isobutyrylamino is especialy preferable.

As the alkoxy group represented by the group —X—$R^{43}$ wherein X is O and $R^{43}$ is the optionally substituted branched alkyl group, a branched $C_{3-13}$ alkoxy group is preferable, and the examples of the branched alkoxy group include isopropoxy, isobutoxy, sec-butoxy, tert-butoxy, isopentyloxy, sec-pentyloxy, tert-pentyloxy, 3-pentyloxy, neopentyloxy, isohexyloxy, sec-hexyloxy, tert-hexyloxy, isooctyloxy, sec-octyloxy, tert-octyloxy, indanyloxy, 4-piperidinyloxy. As preferable examples of the branched alkoxy group, mention is made of $C_{3-9}$ branched alkoxy group, $C_{3-8}$ branched alkoxy group and $C_{3-7}$ branched alkoxy group. Among them, isopropoxy, sec-butoxy, 3-pentyloxy and 2,4-dimethyl-3-pentyloxy are especially preferable.

As the branched alkyl group in the formula: —X—$R^{43}$, wherein X is O, mention is made of $C_{3-13}$ branched alkyl group which includes isopropyl, isobuthyl, sec-buthyl, tert-buthyl, isopentyl, sec-pentyl, tert-pentyl, 3-pentyl, neopentyl, isohexyl, sec-hexyl, tert-hexyl, iso-octyl, sec-octyl and tert-octyl. Preferble examples of the branched alkyl group include branched $C_{3-9}$ alkyl group, branched $C_{3-8}$ alkyl group, branched $C_{3-7}$ alkyl group and branched $C_{3-6}$ alkyl group.

As the substituents on the branched alkyl group, mention is made of those mentioned above in the group of $R^{41}$. Examples of the optionally substituted branched alkyl group include 1,3-difluoro-2-propyl, 1,3-bis(dimethylamino)-2-propyl, 1.3-dimethoxy-2-propyl. Furthermore, examples of the optionally substituted branched alkyl group include 2-indanyl, 4-piperidinyl, N-methyl-4-piperidinyl, dicyclohexylmethyl.

As the cycloalkyl group in the optionally substituted cycloalkyl group of $R^{43}$ in the group of —X—$R^{43}$ wherein X is O, and substituents on the cycloalkyl, mentions are made of those described in the group $R^{41}$ and $R^{42}$.

Examples of the optionally substituted cycloalkyl group include 2,6-dimethyl-1-cyclohexyl, 3,5-dimethyl-1-cyclohexyl, 4-methyl-1-cyclohexyl, 4-ethylcyclohexyl, 4-amino-1-cyclohexyl.

Examples of the 6-membered oxgen-containing heterocyclic group shown in the above includes pyranyl, tetrahydropyranyl, dioxanyl, oxazinyl and isoxazinyl. The heterocyclic group includes an hydrogen additive.

Examples of substituents, which the heterocyclic groups may have, (1)$C_{1-6}$ alkyl, e.g. methyl, ethyl, propyl, isopropyl, n-butyl, isobutyl, sec-butyl, tert-butyl; (2)$C_{1-6}$ alkoxy, e.g. methoxy, ethoxy, propoxy, iso-propoxy, n-butoxy, iso-butoxy, sec-butoxy, tert-butoxy; (3)carbamyol; (4)halogen, e.g. fluorine, chlorine, bromine, iodine; (5)oxo; (6)hydroxy; (7)amino, (8)mono- or di-$C_{1-4}$ alkylamino, e.g. methylamino, ethylamino, propylamino, isopropylamino, butylamino, dimethylamino, diethylamino, dipropylamino, diisopropylamino, dibutylamino; (9)nitro; (10)cyano; (11)mercapto; (12)sulfo; (13)sulfino; (14)$C_{1-6}$ alkylthio, e.g. methylthio, ethylthio, propylthio, isopropylthio, n-butylthio, sec-butylthio, tert-butylthio. The numbers of the substituents are preferably 1 to 6, more preferably 1 to 3, still more preferably 1 or 2.

As preferable examples of substituents on the heterocyclic group, mention is made of halogen, nitro, amino, mono- or di-$C_{1-4}$ alkylamino, oxo, hydroxy, $C_{1-6}$ alkyl (especially, $C_{1-4}$ alkyl), $C_{1-6}$ alkoxy, (especially, $C_{1-4}$ alkoxy), $C_{1-8}$ alkylthio (especially, $C_{1-4}$ alkylthio).

As the alkyl group in the optionally substituted alkyl group of $R^{43}$ in the group of —X—$R^{43}$ wherein X is S, and substituents on the alkyl, mentions are made of those described in the group $R^{41}$, $R^{42}$, $R^{43}$ and $R^{44}$.

As the cycloalkyl group in the optionally substituted cycloalkyl group of $R^{43}$ in the group of —X—$R^{43}$ wherein X is S, and substituents on the cycloalkyl, mentions are made of those described in the group $R^{41}$ and $R^{42}$.

As the 6-membered oxgen-containing heterocyclic group in the optionally substituted 6-membered oxgen-containing heterocyclic group of $R^{43}$ in the group of —X—$R^{43}$ wherein X is S, and substituents on the heterocyclic group, mentions are made of those described in the group $R^{43}$ and $R^{44}$.

In the compound (I), as preferable examples of the group $R^2$, mention is made of (E) a group of the formula: —X—$R^{44}$, wherein when X is O, $R^{44}$ is an optionally substituted branched $C_{3-13}$ alkyl group, an optionally substituted $C_{3-10}$ cycloalkyl group or an optionally substituted 6-membered oxygen-containing heterocyclic group, and when X is S, $R^{44}$ is an optionally substituted $C_{1-13}$ alkyl group, an optionally substituted $C_{3-10}$ cycloalkyl group or an optionally substituted 6-membered oxgen-containing heterocyclic group, or (2) a hydroxyl group;

(F)(1) a group of the formula: —O—$R^{51}$, $R^{51}$ is (1) a branched $C_{3-8}$ alkyl group which may be substituted with $C_{1-4}$ alkyl, (ii) a $C_{3-8}$ cycloalkyl or (iii) a 6-membered oxygen-containing heterocyclic group, (2) a group of the formula: —S—$R^6$, wherein $R^6$ is (1) a $C_{1-6}$ alkyl group, (ii) a $C_{3-8}$ cycloalkyl group or (iii) a 6-membered oxgen-containing heterocyclic group or (3) hydroxyl group; (G) a group of the formula: —O—$R^{51}$, wherein $R^{51}$ is a branched $C_{3-7}$ alkyl group or a 6-membered oxygen-containing heterocyclic group.

Furthermore, in the compound (I), as preferable examples of the group $R^2$, mention is made of a group of the formula: —X—$R^{44}$, wherein X is O, $R^{44}$ is an optionally substituted branched $C_{3-13}$ alkyl group or an optionally substituted 6-membered oxygen-containing heterocyclic group; a group of the formula: —X—$R^{44}$, wherein X is O, $R^{44}$ is a branched $C_{3-13}$ alkyl group which may optionally be substituted with $C_{1-3}$ alkyl or halogen or (2) a 6-membered oxygen-containing heterocyclic group which may optionally be substituted with halogen, $C_{1-4}$ alkoxy, $C_{1-4}$ alkyl or $C_{1-4}$ alkylthio.

In addition to the above, preferable example of the group $R^{44}$ is mentioned as optionally substituted branched $C_{3-7}$ cycloalkyl group or an optionally substituted 6-membered oxygen-containing heterocyclic group.

Preferable example of the group $R^{44}$ includes (1) a branched $C_{3-13}$ alkyl group substituted with $C_{1-3}$ alkyl or halogen atom or (2) a 6-membered oxygen-containing heterocyclic group substituted with halogen, $C_{1-4}$ alkoxy, $C_{1-4}$ alkyl or $C_{1-4}$ alkylthio.

Preferable substituents on the $C_{1-13}$ branched alkyl group of $R^{44}$ or on the $C_{1-13}$ alkyl group of $R^{44}$ include $C_{1-4}$ alkyl, halogen, amino, mono- or di-$C_{1-4}$ alkylamino, $C_{1-4}$ alkoxy or $C_{3-7}$ cycloalkyl. Preferable substituents on the $C_{3-10}$ cycloalkyl group include halogen, nitro, $C_{1-4}$ alkyl, $C_{1-4}$ alkoxy, amino or mono- or di-$C_{1-4}$ alkylamino. Preferable substituents on the optionally suibstituted 6-membered oxygen-containing heterocyclic group include halogen, nitro, oxo, hydroxy, amino, mono- or di-$C_{1-4}$ alkylamino, $C_{1-4}$ alkoxy, $C_{1-4}$ alkyl or $C_{1-4}$ alkylthio.

Specifically preferable examples of the optionally substituted $C_{3-13}$ branched.alkyl is isopropoxy, sec-butoxy, 3-pentyloxy, or 2,4-dimethyl-3-pentyloxy.

As the group $R^2$, specifically preferable examples include ethoxy, isopropoxy, sec-butoxy, 3-pentyloxy, 2,4-dimethyl-3-pentyloxy, tetrahydropyranyloxy, ethylthio, isopropylthio, tetrahydropyranylthio. Among others, isopropoxy, sec-butoxy, 3-pentyloxy, 2,4-dimethyl-3-pentyloxy are more specifically preferable.

The number of the substituents in the group $R^2$, 1 to 3 is preferable and 1 to 2 is more preferable.

As the alkyl group in $R^3$, $C_{1-6}$ alkyl group is preferable, and the examples of it is the same as those mentioned above. In particular, $C_{1-4}$ alkyl and $C_{1-3}$ alkyl are more preferable, and methyl and ethyl are still more preferable.

Concrete examples of the groups $R^{11}$, $R^{12}$ and $R^{13}$ include those mentioned as $R^1$. Concrete examples of the groups $R^{21}$ to $R^{29}$ include those mentioned as $R^2$. Concrete examples of the alkyl group in $R^{31}$ include those mentioned as $R^3$. Concrete examples of the groups $R^{41}$ to $R^{45}$ include those mentioned as $R^4$. Concrete examples of the groups $R^5$, $R^{51}$ and $R^6$ include those mentioned as $R^4$.

In the present specification, the following compounds are disclosed: Ethyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate] or its salt. Ethyl [4,7-dihydro-7-(2,6-difluorobenzyl)-3-(N-benzyl-N-methylaminomethyl)-2-(4-isobutyrylaminophenyl)-6-ethyl-4-oxothieno[2,3-b]pyridine-5-carboxylate] or its salt.

The compound of this invention can be produced by a per se known methods, for example, the methods disclosed in PCT International Publication No. WO 95/28405, the methods mentioned below, analogous methods thereto, or a combination of these method.

Production Method 1:

The compound (I), wherein the group at the 2-position is a phenyl group which is substituted with an alkoxy group substituted with a group selected from the group consisting of (i) halogen, (ii) cycloalkyl and (iii) alkenyl which may optionally be substituted with alkyl, is produced by allowing a 4,7-dihydro-4-oxo-thieno[2,3-b]pyridine derivative, wherein the 2-position is a phenyl group which is substituted with a hydroxyl group, to react with a compound represented by the formula $R^{12}$—Y, wherein $R^{12}$ is the same meaning as defined above, i.e. an alkyl group optionally substituted with (i) halogen, (ii) cycloalkyl or (iii) alkenyl which may optionally be substituted with alkyl and Y stands for a halogen atom, or a salt thereof.

The starting compound can be produced by a method analogous to the method disclosed in PCT International Publication No. WO 95/28405, As examples of the compound represented by the formula $R^{12}$—Y, mention is made of allyl bromide, cyclopropylmethyl chloride, 1-bromo-2-butene, 1-bromo-3-butene, crotyl chloride (i.e. 1-bromo-2-methyl-2-propene), 2,2,2-trifluoroethyl iodide, and so on, or a its salt.

As the alkyl group of $R^{12}$, mention is made of a group which have a structure that an oxygen atom has been eliminated from the alkoxy group shown by $R^1$.

This reaction is conducted usually in a solvent, as exemplified by amides such as dimethylformamide, dimethylacetamide, etc., nitrites such as acetonitrile, etc., and ethers such as ethylether, dioxane, dimethoxyethane, tetrahydrofuran.

This reaction is conducted by dissolving the starting compound in any of these solvents and by adding to the solution a compound represented by the formula $R^{12}$—Y or a salt thereof and a basic compound, e.g. potassium carbonate, sodium carbonate, sodium hydrogencarbonate, sodium hydride, thallium hydride or triethylamine.

The reaction temperature ranges from about 0 to 100° C. preferably from about 0 to 40° C. The reaction time ranges from about 1 to 200 hours, preferably from about 1 to 48 hours. This reaction can be efficiently carried out by stirring.

Production Method 2:

The present compound (I) of the formula (I) mentioned in the above, wherein the group $R^1$ is alkanoylamino-phenyl group, is produced by allowing a 4,7-dihydro-4-oxothieno [2,3-b]pyridine derivative wherein the 2-position is a phenyl group substituted with an amino group to react with a compound represented by the formula $R^{13'}$—Y, wherein $R^{13'}$ stands for $C_{1-8}$ alkanoyl group, the alkanoyl group being that in the "alkanoylamino" group mentioned above and Y stands for a halogen atom, or a salt thereof.

The starting compound can be produced by a method analogous to the method disclosed in PCT International Publication No. WO 95/28405.

This reaction is conducted usually in a solvent, as exemplified by a halogenated solvent such as anhydrous methylene chloride, amides such as dimethylformamide, dimethylacetamide, nitriles such as acetonitrile, ethers such as tetrahydrofuran, ethyl ether, dioxane and dimethoxy ethane.

This reaction is conducted by dissolving the starting compound in any of these solvents and by adding to the solution a compound represented by the formula $R^{13'}$—Y, wherein $R^{13}$ and Y have the same meaning as defined above or a salt thereof, and a basic compound, e.g. potassium carbonate, sodium carbonate, sodium hydrogencarbonate, sodium hydride, triethylamine, potassium-t-butoxide or thallium hydroxide.

The reaction temperature ranges from about 0 to 100° C. preferably from about 0 to 40° C. The reaction time ranges from about 10 minutes to 24 hours, preferably from about 30 minutes to 2 hours. This reaction can be conducted efficiently by stirring.

Production Method 3:

The present compound (I), which has a group of the formula: —CO—$R^{27}$, wherein the group $R^{27}$ is an alkl group or an aryl group, is produced by allowing a 4,7-dihydro-4-oxothieno[2,3-b]pyridine derivative wherein the 5-position is an ester group to a reaction in which the ester compound is converted to a carboxylic acid amide derivative, and then thus obtained carboxylic acid amide derivative is reacted with a Grignard reagent. These reactions are carried out with the similar procedures described in PCT International Publication No. WO 95/28405.

Production Method 4:

The compound (I) wherein $R^2$ stands for an optionally substituted branched alkoxy group, an optionally substituted cycloalkyl group or an optionally substituted heterocyclic group, is produced by subjecting a 4,7-dihydro-4-oxothieno [2,3-b]pyridine derivative which has straight-chain alkoxy-carbonyl group at 5-position to an ester interchange reaction with a compound of the formula: $R^{24}$—H, wherein $R^{24}$ has the same meaning as defined above.

This reaction is conducted usually in a solvent, as exemplified by alcohols such as methanol, ethanol, isopropyl alcohol, 3-pentyl alcohol.

This reaction is carried out by dissolving the starting compound in any of these solvents and then by adding to the solution a compound represented by the formula $Ti(R^{28})_4$, wherein $R^{28}$ is an optionally substituted alkoxy group (Examples of which has the same as those mentioned above.). Examples of the compound are titan(IV) tetraisopropoxide and so forth.

The reaction temperature ranges from about 0 to 120° C. preferably from about 0 to 40° C., more preferably from about 10 to 20° C. The reaction time ranges from about 1 to 24 hours, preferably from about 1 to 12 hours, more preferably from about 1 to 6 hours. This reaction can be conducted efficiently by stirring.

Production Method 5:

The compound (I) wherein $R^2$ stands for a group of the formula: —S—$R^{25}$, wherein $R^{25}$ is optionally substituted alkoxy group (which includes branched alkoxy group), an optionally substituted cycloalkyl group or an optionally substituted heterocyclic group, is produced by reacting a 4,7-dihydro-4-oxothieno[2,3-b]pyridine derivative which has the group —CO—$R^2$, wherein $R^2$ is a straight-chain alkoxy group or a hydroxyl group, at 5-position or a salt thereof with a compound of the formula: $R^{25}$—SH, wherein $R^{25}$ has the same meaning as defined above.

This reaction is conducted with or without a solvent. As the solvent, halogenated solvents such as dichloromethane and so forth are exemplified.

This reaction is carried out in the presence of Vilsmeier reagent, which has been prepared from dimethylformamide and phosphorous oxychloride, under basic conditions such as by adding for example N,N-dimethylaminopyridine.

The reaction temperature ranges from about 0 to 200° C., preferably from about 0 to 120° C. The reaction time ranges from about 1 to 24 hours, preferably from about 2 to 12 hours.

This reaction can be conducted efficiently by stirring.

Production Method 6:

The compound (I) wherein —CO—$R^2$ is carboxyl group, is produced by subjecting the compound (I) wherein $R^2$ is alkoxy group or a salt thereof, which is produced by the method disclosed in the PCT International Publication WO 95/28405 or an analogous method thereto, to hydrolysis.

The hydrolysis is conducted in a solvent such as ethers, e.g. tetrahydrofuran and dioxane, alcohols, e.g. ethyl alcohol, methyl alcohol.

In this reaction, it proceeds smoothly in the presence of an acid, e.g. inorganic acid such as hydrochloric acid (e.g. 2N aqueous solution is preferable) or an aqueous alkaline solution, e.g. an aqueous solution of alkali metal hydroxide such as sodium hydroxide, potassium hydroxide or lithium hydroxide (a 1N to 4N aqueous solution of the alkali is preferable).

The reaction temperature ranges from about 10 to 100° C. preferably 20 to 60° C. The reaction time ranges from about 1 to 4 hours, preferably 2 to 4 hours. The reaction is conducted efficiently by stirring.

Production Method 7:

The compound (I) wherein $R^2$ stands for an optionally substituted alkoxy group (which includes branched alkoxy group), an optionally substituted cycloalkyl-oxy group or an optionally substituted heterocyclic group-oxy group, is produced by reacting a 4,7-dihydro-4-oxothieno[2,3-b]pyridine derivative which has the group —CO—$R^2$, wherein —CO—$R^2$ is carboxyl group, at 5-position or a salt thereof with a compound of the formula: $R^{29}$—OH, wherein $R^{29}$ is an optionally substituted alkyl group (which includes branched alkyl group), an optionally substituted cycloalkyl group or an optionally substituted heterocyclic group, for example isopropanol, 2,4-dimethyl-3-pentanol.

This reaction is conducted with or without a solvent. As the solvent, halogenated solvents such as dichloromethane and so forth are exemplified.

This reaction is carried out in the presence of Vilsmeier reagent, which has been prepared by dimethylformamide and phosphorous oxychloride, under basic conditions by adding for example N,N-dimethylaminopyridine. The reaction temperature ranges from room temperature to heating (about 100° C.) preferably from about 0 to 120° C. The reaction time ranges from about 1 to 12 hours, preferably from about 4 to 12 hours. This reaction can be conducted efficiently by stirring.

Production Method 8:

The compound (IX), in which the group $R^3$ is an alkyl group, is produced by reacting a compound of 4,7-dihydro-4-oxothieno[$_{2,3}$-b]pyridine derivative (VIII) wherein $R^2$ is a group of the formula: —X—$R^4$, wherein X and $R^4$ have the same meanings as defined above, $R^3$ is hydrogen, or its salt, with a compound of the formula: $R^{32}$—Z, wherein $R^{32}$ and Z have the same meanings as defined above.

Examples of metals of the group Z in the compound of the formula: $R^{32}$—Z include magnesium and lithium. The halogen includes chloride, bromide. The halogenated metals include Grignard reagents (e.g. methylmagnesium chloride, ethylmagnesium chloride), and lithium chloride.

This reaction is conducted usually in a solvent, as exemplified by halogenated hydrocarbons, e.g. dichloromethane, ethers, e.g. tetrahydrofuran, ethylether, dioxane, dimethoxyethane. This reaction proceeds smoothly in the presence of copper salt, e.g. copper iodide.

The reaction temperature ranges from about 0 to 80° C. preferably 0 to 40° C. The reaction time ranges from about 0.5 to 24 hours, preferably 0.5 to 2 hours. The reaction is conducted efficiently by stirring.

As salts of the present compound (I), physiologically acceptable acid addition salts are preferable. Examples of such salts includes those with an inorganic acid, e.g. hydrochloric acid, hydrobromic acid, nitric acid, sulfuric acid and phosphoric acid, or those with an organic acid, e.g. formic acid, acetic acid, trifluoroacetic acid, fumaric acid, oxalic acid, tartaric acid, maleic acid, citric acid, succinic acid, malic acid, methanesulfonic acid, benzenesulfonic,acid, and p-toluenesulfonic acid. Further, when the compound (I) has an acid group such as —COOH, the compound (I) may form a salt with an inorganic base, e.g. an alkali metal or alkaline earth metal such as sodium, potassium, calcium and magnesium; ammonia, or an organic base, e.g. trimethylamine, triethylamine, pyridine, picoline, ethanolamine, diethanolamine, triethanolamine, dicyclohexylamine and N,N'-dibenzylethylenediamine. The present compound (I) or its salt may also be in the form of hydrates thereof, e.g. 1 hydrate, 1.5 hydrates or 2 hydrates.

The present compound (I), its salt or their hydrates produced thus above can be isolated and purified by a conventional separating and/or purifying means such as recrystallization, distillation and chromatography. In the case where the compound (I) is produced in a free form, it can be converted to a salt thereof by a per se conventional means or a method analogous thereto. On the contrary, when it is obtained in the form of a salt, it can be converted to its free form or to any other salt. In the case where the compound or a salt thereof of the present invention is an optically active compound, it can be separated into d-compound and l-compound by means of a conventional optical resolution.

Since the compound (I) or its salt of this invention, hereinafter it is sometimes abbreviated as "the present compound", have a GnRH antagonistic activity and excellent properties such as oral administrabilty (namely, high bioavailability when orally administered), stability in plasma of blood and durability of actions as well as less toxicity, the present compound can be safely used for the therapy of male hormone or female hormone dependent diseases as well as the therapy of diseases caused by excess secretion of these hormones, in mammals, e.g. human, monkey, cow, horse, dog, cat, rabbit, rat and mouse, suppressing the secretion of gonadotropic hormone by the action of GnRH receptor antagonistic action.

More specifically, the present compound is effective as a prophylactic or therapeutic agent for the prevention or treatment of several hormone dependent diseases, for example, a sex hormone dependent cancer (e.g. prostate cancer, cancer of the uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris. And, the present compound is also effective as a fertility controlling agent in both sexes, e.g. pregnancy controlling agents and menstrual cycle controlling agents. The present compound can be further used as a contraceptive of male or female and, as an ovulation-inducing agent of female. The present compound can be used as an infertility treating agent by using a rebound effect owing to a stoppage of administration thereof. Further, the present compound is useful as modulating estrous cycles in animals in the field of animal husbandry, and as an agent for improving the quality of edible meat or promoting the growth of animals. Besides, the present compound is useful as an agent of spawning promotion in fish.

While the present compound can be used singly, they can also effectively be used by administering in combination with a steroidal or non-steroidal antiandrogenic agent. The present compound can effectively be used by administering in combination with a chemotherapeutic agent for cancer. In treatment of prostate cancer, examples of the chemotherapeutic agent include Ifosfamide, UFT, Adriamycin, Peplomycin, Cisplatin and the like. In treatment of breast cancer, examples of the chemotherpeutic agent include Cyclophosphamide, 5-FU, UFT, Methotrexate, Adriamycin, Mitomycin C, Mitoxantrone and the like.

When the present compound is employed as prophylactic and/or therapeutic agents of the above-mentioned diseases, the present compound can be administered orally or parenterally in accordance with per se known means. It is mixed with a pharmaceutically acceptable carrier, excipient or diluent therefor and usually administered orally as a solid preparation such as tablet, capsule, granule or powder, or parenterally as intravenous, subcutaneous or intramuscular injection, or as suppository or sublingually administrable tablet. Further, it is sublingually, subcutaneously or intramuscularly administered as a sustained release formulation such as sublingually administrable tablets, or microcapsules.

The daily dose of the present compound varies with the degree of affliction; age, sex, body weight and difference of sensitivity of the subject to be administered; the time and intervals of administration, properties,-dosage forms and kinds of the medicinal preparation; and kinds of the effective components, and it ranges usually, though not specifically limited, from about 0.1 to 30 mg, preferably from about 0.1 to 3 mg, more preferably from about 0.1 to 1 mg, relative to 1 kg body weight of the mammals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.01 to 5 mg, preferably from about 0.03 to 3 mg, once or 2 to 3 divided dosages.

As the above-mentioned pharmaceutically acceptable carriers, excipients or diluents therefor, conventional various organic or inorganic carriers excipients or diluents are used, and they are incorporated as excipients, lubricants, binders and disintegrants in solid compositions; and as solvents, solubilisers, suspending agents, isotonizing agents, buffering agents and pain-easing agents in liquid or solid compositions. And, depending on necessity, further additives such as preservatives, anti-oxidants, coloring agents and sweeteners can also be used.

Preferable examples of the above-mentioned excipients include lactose, sugar, D-mannitol, starch, crystalline cellulose and light anhydrous silicic acid. Preferable examples of above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxypropylmethyl cellulose, polyvinyl pyrrolidone and polyethylene glycol. Preferable examples of the above-mentioned disintegrants include starch, carboxymethyl cellulose, carboxymethyl cellulose calcium, low substituted hydroxypropyl cellulose, cross carmelose sodium and carboxymethyl starch sodium.

Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, tris-aminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glucose, glycerin, D-mannitol and D-sorbitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned antioxidants include sulfite and ascorbic acid. Preferable examples of the above coloring agent include red iron oxide and titanium oxide.

To the compound of this invention, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method. Examples of the above-mentioned pharmaceutical composition are orally administering agents, e.g. diluted powders, granules, capsules and tablets; injections; dropping injections; external agents, e.g. transnasal preparations, percutaneous preparations, etc.; ointments, e.g. rectal ointment, vaginal ointment, etc. and the like. Such pharmaceutical compositions can be manufactured by a per se known method commonly used in preparing pharmaceutical compositions.

Concretely, the present compound can be made into injections either in a form of an aqueous injection together with dispersing agents, e.g. Tween 80 (Atlas Powder, U.S.A.), HCO 60 (Nikko Chemicals, Japan), polyethylene glycol, carboxymethylcellulose, sodium alginate, etc., preservatives, e.g. methyl paraben, propyl paraben, benzyl alcohol, etc., isotonizing agents, e.g. sodium chloride, mannitol, sorbitol, glucose, etc. and the like or in a form of an oily injection by dissolving, suspending or emulsifying in plant oil, e.g. olive oil, sesame oil, cotton seed oil, corn oil, etc.; propylene glycol and the like. In preparing a pharmaceutical composition for oral use, the present compound is molded by compressing, for example, with excipients, e.g. lactose, sucrose, starch, etc.; disintegrating agents, e.g. starch, calcium carbonate, etc.; binders, e.g. starch, gum arabic, carboxymethylcellulose, polyvinylpyrrolidone, hydroxypropylcellulose, etc.; or lubricants, e.g. talc, magnesium stearate, polyethylene glycol 6000, etc. and the like.

If necessary, the present composition is coated by a per se known method with an object of masking the taste, enteric coating or long-acting sustained release. Examples of the coating agent therefore are hydroxypropylmethylcellulose, ethylcellulose, hydroxymethylcellulose, hydroxypropylcellulose, polyoxyethylene glycol, Tween 80, Pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), coloring agent, e.g. red iron oxide, titanium oxide and the like. Subcoating layer may be provided between the enteric coating and the core according to a per se known method.

In preparing an external composition, the present compound as it is or a salt thereof is subjected to a per se known method to give a solid, semisolid or liquid agent for external use. For example, the solid preparation is manufactured as follows. The present compound as it is or after adding/mixing excipients, e.g. mannitol, starch, microcrystalline cullulose, etc., thickeners, e.g. natural gums, cellulose derivatives, acrylic acid polymers, etc. and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be as compounded with a pH adjusting agent, e.g. carbonic acid, phosphoric acid, citric acid, hydrochloric acid, sodium hydroxide, etc., an antiseptic agent, e.g. p-hydroxybenzoates, chlorobutanol, benzalkonium chloride, etc. and the like. In the manufacture of an ointment for zori example, the present compound can be made into an oily or an aqueous solid, semisolid or liquid ointment. Examples of the oily base material applicable in the above-mentioned composition are glycerides of higher fatty acids, e.g. cacao butter, Witepsols (manufactured by Dynamite-Nobel), etc., medium fatty acids, e.g. Miglyols (manufactured by Dynamite-Nobel), etc.; and plant oil, e.g. sesame oil, soybean oil, cotton seed oil, etc. and the like. Examples of the aqueous base material are polyethylene glycols and propylene glycol and those of the base material for aqueous gel are natural gums, cellulose derivatives, vinyl polymers, acrylic acid polymers, etc.

BESST MODE FOR CARRYING OUT THE INVENTION

By way of the following Reference Examples and Examples, the present invention will be described in more detail, but they are not intended to limit the scope of the invention.

$^1$H-NMR spectra were taken with JEOL LAMBDA 300 (300 MHz) type spectrometer, employing tetramethylsilane as the internal standard. All data values were expressed in ppm.

The symbols used in the present specification have the following meanings:

s: singlet, d: doublet, t: triplet, dt: double triplet, m: multiplet, br: broad.

REFERENCE EXAMPLE 1

(1) Production of 4,7-dihydro-7-(2,6-difluorobenzyl)-2-(4-hydroxyphenyl)-3-methyl-4-oxothieno[2,3-b]pyridine-5-carboxylic acid ethyl ester:

The compound produced in accordance with Working Example 3(10) of PCT International Publication No. WO 95/28405, i.e. 7-(2,6-difluorobenzyl)-2-(4-methoxyphenyl)-3-methyl-4-oxothieno[2,3-b]pyridine-5-carboxylic acid ethyl ester (3.0 g, 6.39 mmol), was dissolved in dichloromethane (30 ml), and to which was added dropwise, under ice-cooling, a dichloromethane solution (40 ml) of aluminum chloride (4.27 g, 32 mmol) and dimethyl disulfide (2.88 ml, 32 mmol). The mixture was stirred for 4 hours at the same temperature, then the reaction mixture was concentrated to dryness. The concentrate was partitioned between ethyl acetate and a saturated aqueous solution of sodium hydrogen carbonate. The organic layer was washed with water, followed by concentration to dryness. The concentrate was recrystallized from ethanol-ethyl acetate to give the titled compound as pale yellow powdery crystals (1.64 g, 56%).

m.p. 244–246° C.

Elemental Analysis for $C_{24}H_{19}F_2NO_4S.0.2H_2O$:

|  | C (%) | H (%) | N (%) |
|---|---|---|---|
| Calcd.: | 62.79; | 4.26; | 3.05 |
| Found: | 62.80; | 4.11; | 3.14 |

$^1$H-NMR (300 MHz, CDCl$_3$)δ: 1.40(3H,t,J=7.2 Hz), 2.64 (3H,s), 4.40(2H,q,J=7.2 Hz), 5.26(2H,s), 6.96–7.02(4H,m), 7.25–7.28(2H,m), 7.31–7.46(1H,m), 8.40(1H,s).

(2) Production of 4,7-dihydro-7-(2,6-difluorobenzyl)-2-(4-methoxymethoxyphenyl)-3-methyl-4-oxothieno[2,3-b] pyridine-5-carboxylic acid ethyl ester:

The compound produced in Reference Example 1(1) (1.6 g, 3.51 mmol) was dissolved in dimethylformamide (20 ml). To the solution was added, under ice-cooling, sodium hydride (0.154 g, 3.86 mmol), and the mixture was stirred for 30 minutes. To the reaction mixture was added, at the same temperature, chloromethyl methylether (0.324 ml, 4.21 mmol). The mixture was stirred for 30 minutes at the same temperature and, then, for 2 hours at room temperature. To the reaction mixture was added ethanol (10 ml), which was concentrated to dryness. The concentrate was partitioned between dichloromethane and a saturated aqueous sodium chloride solution. The organic layer was washed with water and concentrated to dryness. The concentrate was purified by means of a silica gel column chromatography to give the titled compound as an amorphous product (1.63 g, 93%).

Elemental Analysis for $C_{26}H_{23}F_2NO_5S.0.38H_2O$:

|  | C (%) | H (%) | N (%) |
|---|---|---|---|
| Calcd.: | 61.67; | 4.73; | 2.77 |
| Found: | 61.42; | 4.57; | 3.07 |

$^1$H-NMR (300 MHz, CDCl$_3$)δ: 1.41(3H,t,J=7.2 Hz), 2.65 (3H,s), 3.50(3H,s), 4.40(2H,q,J=7.2 Hz), 5.22(2H,s), 5.25 (2H,s), 7.00(2H,t,J=8.3 Hz), 7.10(2H,d,J=6.8 Hz), 7.33–7.41(3H,m), 8.37(1H,s).

(3) Production of 4,7-dihydro-7-(2,6-difluorobenzyl)-2-(4-methoxymethoxyphenyl)-3-(N-benzyl-N-methylaminomethyl)-4-oxothieno[2,3-b]pyridine-5-carboxylic acid ethyl ester:

The compound produced in the above-mentioned Reference Example 1(2) (5.60 g, 11.2 mmol) was suspended in carbon tetrachloride (100 ml). To the suspension were added N-bromosuccinic acid imide (2.19 g, 12.3 mmol) and α,α'-azobisisobutyronitrile (0.37 g, 2.24 mmol). The mixture was heated for 2 hours under refluxing. The reaction mixture was cooled to room temperature, to which was added dichloromethane (100 ml). The mixture was washed with a saturated aqueous saline solution and dried, followed by concentration to dryness. The concentrate was dissolved in dimethylformamide (100 ml). To the solution were added ethyl diisopropylamine (2.10 ml, 12.3 mmol) and N-methylbenzylamine (1.59 ml, 12.3 mmol). The mixture was stirred for two hours, followed by concentration to dryness. The concentrate was partitioned between dichloromethane and water. The organic layer was washed with a saturated aqueous sodium chloride solution, dried and concentrated to dryness to give a solid matter, which was purified by means of a silica gel column chromatography to give the titled compound as an amorphous product (6.35 g, 92%).

Elemental Analysis for $C_{34}H_{32}F_2N_2O_5S.0.5H_2O$:

|  | C (%) | H (%) | N (%) |
|---|---|---|---|
| Calcd.: | 65.06; | 5.30; | 4.46 |
| Found: | 65.28; | 5.22; | 4.49 |

$^1$H-NMR (300 MHz, CDCl$_3$)δ: 1.39(3H,t,J=7.2 Hz), 2.20 (3H,s), 3.51(3H,s), 3.93(2H,s), 4.20(2H,s), 4.40(2H,q,J=7.2 Hz), 5.23(2H,s), 5.27(2H,s), 7.00(2H,t,J=8.3 Hz), 7.10(2H,d,J=6.8 Hz), 7.18–7.26(5H,m), 7.36–7.44(1H,m), 7.72–7.75 (2H,m), 8.37(1H,s).

(4) Production of 4,7-dihydro-7-(2,6-difluorobenzyl)-2-(4-methoxymethoxyphenyl)-3-(N-benzyl-N-methylaminomethyl)-4-oxothieno[2,3-b]pyridine-5-N-methyl-O-methyl-hydroxamic acid:

To a dichloromethane solution (100 ml) of N-methyl-O-methylhydroxylamine hydrochloride (4.98 g, 151 mmol) and N-ethyl diisopropylamine (8.73 ml, 151 mmol) was added, under ice-cooling, trimethyl alminium (1.5N solution, 20.4 ml, 130.6 mmol). The mixture was stirred for 30 minutes at the same temperature, then for further 30 minutes at room temperature.

To the reaction mixture was added, under ice-cooling, a dichloromethane solution (100 ml) of the compound produced in Reference Example 1(3) (6.30 g, 10.2 mmol). The mixture was stirred for further 2 hours at the same temperature. The reaction mixture was poured into water, which was then subjected to extraction with chloroform. The extract was washed with a saturated aqueous sodium chloride solution, dried and concentrated to dryness to give the titled compound as an amorphous product (5.73 g, 89%).

Elemental Analysis for $C_{34}H_{33}F_2N_3O_5S.1.2H_2O$:

|  | C (%) | H (%) | N (%) |
|---|---|---|---|
| Calcd.: | 62.32; | 5.44; | 6.41 |
| Found: | 62.51; | 5.49; | 6.38 |

$^1$H-NMR (300 MHz, CDCl$_3$)δ: 2.21(3H,s), 3.34(3H,s), 3.54(3H,s), 3.72(2H,s), 3.76(3H,s), 4.19(2H,s), 5.23(2H,s), 5.30(2H,s), 6.95(2H,t,J=8.3 Hz), 7.12(2H,d,J=6.8 Hz), 7.15–7.22(5H,m), 7.33–7.41(1H,m), 7.70–7.74(2H,m), 8.33 (1H,s).

(5) Production of 4,7-dihydro-7-(2,6-difluorobenzyl)-2-(4-hydroxyphenyl)-3-(N-benzyl-N-methylaminomethyl)-5-benzoyl-4-oxothieno[2,3-b]pyridine:

The compound produced in the Reference Example 1(4) (5.20 g, 8.20 mmol) was dissolved in anhydrous tetrahydrofuran (100 ml). To the solution was added, under ice-cooling, phenyl magnesium bromide (1M solution, 24.6 ml, 24.6 mmol). The mixture was stirred for 3 hours at the same temperature, to which was added, under ice-cooling, 6N hydrochloric acid to adjust the pH to not higher than 2, followed by stirring for one hour at room temperature. The reaction mixture was neutralized and, then, poured into water, which was then subjected to extraction with ethyl acetate. The extract was washed with a saturated aqueous sodium chloride solution, dried and concentrated to dryness to give the titled compound as an amorphous product (3.37 g, 68%).

Elemental Analysis for $C_{36}H_{28}F_2N_3O_5S$:

|  | C (%) | H (%) | N (%) |
| --- | --- | --- | --- |
| Calcd.: | 71.27; | 4.65; | 4.62 |
| Found: | 71.20; | 4.58; | 4.70 |

$^1$H-NMR (300 MHz, CDCl$_3$)δ: 2.37(3H,s), 3.91(2H,s), 4.30(2H,s), 5.38(2H,s), 6.98–7.05(4H,m), 7.21–7.38(5H,m), 7.43–7.48(5H,m), 7.55–7.59(1H,m), 7.90(2H,d,J=7.1 Hz), 8.06(1H,s).

(6) Production of 4,7-dihydro-7-(2,6-difluorobenzyl)-2-(4-hydroxyphenyl)-3-(N-benzyl-N-methylaminomethyl)-5-isobutyryl-4-oxothieno[2,3-b]pyridine:

Employing the compound produced in Reference Example 1(4) as the starting material, the titled compound was produced as an amorphous product (2.1 g, 51%) by substantially the same procedure as in Reference Example 1(5) using isopropyl magnesium chloride in place of phenyl magnesium bromide.

$^1$H-NMR (300 MHz, CDCl$_3$)δ: 1.18(6H,d), 2.10(3H,s), 3.61(2H,s), 4.1–4.2(3H,m), 5.26(2H,s), 6.90(2H,d), 6.99 (2H,t), 7.1–7.2(6H,m), 7.40(1H,m), 7.65(2H,d), 8.28(1H,s).

REFERENCE EXAMPLE 2

The compound produced in Reference Example 1(3) is subjected to hydrolysis in tetrahydrofuran by adding a little excess amount of 1N sodium hydroxide while stirring for 2 hours at room temperature, to thereby convert the compound into a compound whose substituent at 5-position is carboxyl group (a carboxylic acid derivative).

The carboxylic acid derivative is mixed, in dimethylformamide, with N,N-dimethylaminopyridine (large excess amount) and alcohol (e.g. isopropanol, cyclohexanol, sec-butanol, 3-pentanol or 2,4-dimethyl-3-pentanol). To the mixture is added dropwise, under ice-cooling, phosphorus oxychloride (10 times as much volume) to produce a compound whose substituent at 5-position is an ester.

The ester derivative is subjected to a conventional deprotection reaction by using a diluted hydrochloric acid to give the compound 2(1), 2(2), 2(3), 2(4) and 2(5) shown in the below-mentioned Table 1.

The compound obtained by the method of Reference Example 1(3) is subjected to a conventional deprotection reaction by using a diluted hydrochloric acid to give a compound wherein the methoxymthyl group in the methoxymethoxy group of the starting compound is eliminated. The structure of thus obtained compound is shown in the below-mentioned Table 1.

REFERENCE EXAMPLE 3
Production of 4,7-dihydro-7-(2,6-difluorobenzyl)-2-(4-isobutyrylaminophenyl)-3-(N-methyl-N-benzylaminomethyl)- 4-oxothieno[2,3-b]pyridine-5-carboxylic acid ethyl ester:

To the compound produced in accordance with Working Example 27 described in PCT International Publication No. WO95/28405, i.e. 4,7-dihydro-7-(2,6-difluorobenzyl)-2-(4-aminophenyl)-3-(N-methyl-N-benzylaminomethyl)-4-oxothieno[2,3-b]pyridine-5-carboxylic acid ethyl ester, was added, in pyridine, a little excess amount of isobutyryl chloride. The mixture was stirred for 2 hours at room temperature to give the titled compound.

m.p. 185–186° C.

Elemental Analysis for $C_{36}H_{35}F_2N_3O_4S \cdot HCl \cdot 1.5H_2O$:

C(%) H(%) N(%)
Calcd.: 61.14; 5.56; 5.94
Found: 61.00; 5.60; 5.87

$^1$H-NMR (300 MHz, CDCl$_3$)δ: 1.28(6H,d,J=6.8 Hz), 1.39 (3H,t,J=7.1 Hz), 2.12(3H,s), 2.54(1H,m), 3.56(2H,s), 4.16 (2H,s), 4.40(2H,q,J=7.1 Hz), 5.26(2H,s), 7.01(2H,t,J=8.1 Hz), 7.10–7.30(5H,m), 7.41(1H,m), 7.62(2H,d,J=8.5 Hz), 7.81(2H,d,J=8.5 Hz), 8.35(1H,s).

The structures of compounds which were obtained in Reference Examples 1(3) to 1(6) and in Reference Examples 2 and 3 are shown in the following Table 1.

TABLE 1

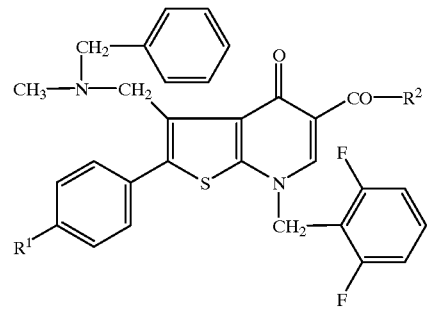

| Ref. No. | R$^1$ | R$^2$ |
| --- | --- | --- |
| 1(3) | methoxymethoxy | ethoxy |
| 1(4) | methoxymethoxy | N-methyl-O-methylhydroxylamino |
| 1(5) | hydroxy | phenyl |
| 1(6) | hydroxy | isopropyl |
| 2(1) | hydroxy | isopropoxy |
| 2(2) | hydroxy | cyclohexyloxy |
| 2(3) | hydroxy | sec-butoxy |
| 2(4) | hydroxy | 3-pentoxy |
| 2(5) | hydroxy | 2,4-dimethyl-3-pentoxy |
| 2(6) | hydroxy | ethoxy |
| 3 | isobutyrylamino | ethoxy |

EXAMPLE 1
Production of 3-(N-methyl-N-benzylaminomethyl)-4,7-dihydro-7-(2,6-difluorobenzyl)-2-(4-allyloxyphenyl)-5-benzoyl-4-oxothieno[2,3-b]pyridine hydrochloride:

To a solution of the compound produced in Reference Example 1(5) (0.12 g, 0.2 mmol) in dimethylformamide (3 ml) were added, under ice-cooling, potassium carbonate (0.055 g, 0.4 mmol) and allyl iodide (37 μl, 0.4 mmol). The mixture was stirred for 2 hours at room temperature, which was then concentrated. The concentrate was partitioned between ethyl acetate and a saturated aqueous sodium chloride solution. The aqueous layer was subjected to extraction with ethyl acetate.

The organic layers were combined and dried (MgSO$_4$), followed by distilling off the solvent under reduced pressure. The residue was purified by means of a silica gel column chromatography to give a colorless oily product. To a solution of this oily product in ether (4 ml) was added, under ice-cooling, 1N hydrogen chloride in ether (0.2 ml). The mixture was stirred for 10 minutes at the same temperature. The reaction mixture was concentrated under reduced pressure. The concentrate was crystallized from ethyl acetate-ether to give the titled compound as a white crystalline product (0.068 g, 50%). The structure of thus obtained compound is shown in the below-mentioned Table 2.

m.p. 120–122° C.

Elemental Analysis for $C_{39}H_{32}F_2N_2O_3S \cdot HCl \cdot 1.5H_2O \cdot 0.1CHCl_3$:

|  | C (%) | H (%) | N (%) |
|---|---|---|---|
| Calcd.: | 65.03; | 5.04; | 3.88 |
| Found: | 65.05; | 4.80; | 3.81 |

$^1$H-NMR (300 MHz, DMSO-$d_6$)δ: 2.83(3H,s), 4.32–4.63 (6H,m), 5.31–5.49(4H,m), 6.02–6.14(1H,m), 7.01–7.09(4H, m), 7.24–7.63(11H,m), 7.95(2H,d,J=7.8 Hz), 8.16(1H,s), 11.95(1H,brs).

EXAMPLE 2

Employing the compound produced in Reference Example 1(5) as the starting material, substantially the same procedure as described in Example 1 is conducted to give compounds 2(1), 2(2), 2(3) and 2(4), whose structures are shown in the below-mentioned Table 2.

EXAMPLE 3

Employing the compound produced in Reference Example 1(6) as the starting material, substantially the same procedure as described in Example 1 was conducted to give compounds 3(1), 3(2), 3(3), 3(4), 3(5) and 3(6), whose structures are shown in the following Table 2.

TABLE 2

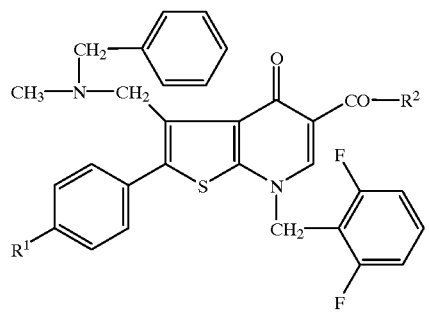

| Ex. No. | R$^1$ | R$^2$ | yield (%) | m.p. (° C.) |
|---|---|---|---|---|
| 1 | allyloxy | phenyl | 50 | 120–122 (hydrochloride) |
| 2(1) | cyclopropylmethoxy | phenyl | | |
| 2(2) | 2-buten-1-yloxy | phenyl | | |
| 2(3) | 2-methyl-2-propen-1-yloxy | phenyl | | |
| 2(4) | 3-buten-1-yloxy | phenyl | | |
| 3(1) | allyloxy | isopropyl | 46 | 182–184 (hydrochloride) |
| 3(2) | cyclopropylmethoxy | isopropyl | 58 | 152–155 (hydrochloride) |
| 3(3) | 2-buten-1-yloxy | isopropyl | 34 | 126–130 (hydrochloride) |
| 3(4) | 2-methyl-2-propen-1-yloxy | isopropyl | 60 | 175–177 (hydrochloride) |
| 3(5) | 3-buten-1-yloxy | isopropyl | 12 | 141–144 (hydrochloride) |
| 3(6) | 2,2,2-trifluoro-ethoxy | isopropyl | 3 | 128–130 (hydrochloride) |

EXAMPLE 4

Employing the compound produced in Reference Example 2 as the starting material, substantially the same procedure as described in Example 1 is conducted to give compounds 4(1) to 4(22), whose structures are shown in the following Table 3.

TABLE 3

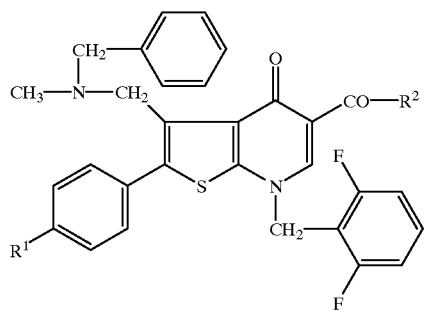

| Ex. No. | R$^1$ | R$^2$ | yield (%) | m.p. (° C.) |
|---|---|---|---|---|
| 4(1) | allyloxy | isopropoxy | 63 | 167–169 (hydrochloride) |
| 4(2) | cyclopropylmethoxy | isopropoxy | | |
| 4(3) | 2-buten-1-yloxy | isopropoxy | | |
| 4(4) | 2-methyl-2-propen-1-yloxy | isopropoxy | | |
| 4(5) | 3-buten-1-yloxy | isopropoxy | | |
| 4(6) | allyloxy | cyclohexyloxy | | |
| 4(7) | cyclopropylmethoxy | cyclohexyloxy | | |
| 4(8) | 2-buten-1-yloxy | cyclohexyloxy | | |
| 4(9) | 2-methyl-2-propen-1-yloxy | cyclohexyloxy | | |
| 4(10) | allyloxy | sec-butoxy | | |
| 4(11) | cyclopropylmethoxy | sec-butoxy | | |
| 4(12) | 2-buten-1-yloxy | sec-butoxy | | |
| 4(13) | 2-methyl-2-propen-1-yloxy | sec-butoxy | | |
| 4(14) | allyloxy | 3-pentoxy | | |
| 4(15) | cyclopropylmethoxy | 3-pentoxy | | |
| 4(16) | 2-buten-1-yloxy | 3-pentoxy | | |

TABLE 3-continued

[Chemical structure diagram showing a thieno[2,3-b]pyridine with CH₃-N(CH₂-phenyl)-CH₂ substituent, 4-R¹-phenyl group, CO-R² group, and N-CH₂-(2,6-difluorophenyl) group]

| Ex. No. | R¹ | R² | yield (%) | m.p. (° C.) |
|---|---|---|---|---|
| 4(17) | 2-methyl-2-propen-1-yloxy | 3-pentoxy | | |
| 4(18) | allyloxy | 2,4-dimethyl-3-pentoxy | | |
| 4(19) | cyclopropylmethoxy | 2,4-dimethyl-3-pentoxy | | |
| 4(20) | 2-buten-1-yloxy | 2,4-dimethyl-3-pentoxy | | |
| 4(21) | 2-methyl-2-propen-1-yloxy | 2,4-dimethyl-3-pentoxy | | |
| 4(22) | allyloxy | ethoxy | | |

EXAMPLE 5
Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid isopropyl ester hydrochloride:

To an isopropyl alcohol solution (50 ml) of the compound obtained in Reference Example 3 (1.29 g, 2.0 mmol) was added dropwise, under ice-cooling (0° C.), titan(IV) isopropoxide (0.284 g, 1.0 mmol). The mixture was stirred for 12 hours at room temperature. The reaction mixture was partitioned between chloroform (200 ml) and water. The aqueous layer was subjected to extraction with chloroform (200 ml). The extract solutions were combined, washed with an aqueous sodium chloride solution and dried ($Na_2SO_4$), followed by distilling off the solvent under reduced pressure. The residue was purified by means of a silica gel column chromatography to give a colorless amorphous product (1.08 g, 82%). The amorphous product thus obtained was dissolved in chloroform. To the solution was added a 10N hydrogen chloride in ethanol solution to form a corresponding salt, which was recrystallized from chloroform-ether to give the titled compound as colorless crystalline needles (0.86 g, 74%). The structure of the compound thus obtained is shown in the below-mentioned Table 4.

m.p. 168–170° C.
Elemental Analysis for $C_{37}H_{37}F_2N_3O_4S\cdot HCl\cdot 0.5H_2O$:

| | C (%) | H (%) | N (%) |
|---|---|---|---|
| Calcd.: | 63.19; | 5.59; | 5.98 |
| Found: | 63.33; | 5.70; | 6.09 |

¹H-NMR (300 MHz, $CDCl_3$)δ: 1.28(6H,d,J=6.8 Hz), 1.36 (6H,d,J=6.3 Hz), 2.10(3H,s), 2.57(1H,m), 3.65(2H,s), 4.16 (2H,s), 5.23(1H,m), 5.23(2H,s), 7.00(2H,dd,J=8.1 Hz), 7.10–7.26(5H,m), 7.38(1H,m), 7.63(2H,d,J=8.3 Hz), 7.78 (2H,d,J=8.6 Hz), 8.29(1H,m).

EXAMPLE 6
Employing the compound obtained in Reference Example 3 as the starting material, the compounds 6(1), 6(2), 6(3) and 6(4) were produced in substantially the same manner as described in Example 5. The structure of these compounds are shown in Table 4.

TABLE 4

[Chemical structure diagram showing a thieno[2,3-b]pyridine with CH₃-N(CH₂-phenyl)-CH₂ substituent, a 4-(isobutyrylamino)phenyl group ((CH₃)₂CH-CO-NH-), CO-R² group, and N-CH₂-(2,6-difluorophenyl) group]

| Ex. No. | R² | yield (%) | m.p. (hydrochloride) (° C.) |
|---|---|---|---|
| 5 | isopropyloxy | 74 | 168–170 |
| 6(1) | sec-butyloxy | 82 | 171–173 |
| 6(2) | cyclohexyloxy | 73 | 177–179 |
| 6(3) | 3-pentyloxy | 78 | 194–195 |
| 6(4) | 4-tetrahydropyranyloxy | 64 | 165–167 |

EXAMPLE 7
Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid:

The compound obtained in Reference Example 3 (1.2 g) was dissolved in ethanol (10 ml), to which was added 5N potassium hydroxide (5 ml) while cooling at 0° C. The reaction mixture was warmed to room temperature, which was stirred for 5 hours, followed by shaking together with 0.2N hydrochloric acid (200 ml) and chloroform (200 ml). From the organic layer, a crystalline product was obtained, which was recrystallized from ethyl acetate-ethanol to give the titled compound as colorless powdery crystals (1.0 g, 81%). The structure of thus obtained compound is shown in the below-mentioned Table 5.

m.p. 212–214° C.
Elemental Analysis for $C_{34}H_{31}F_2N_3O_4S\cdot 2.5H_2O$:

| | C (%) | H (%) | N (%) |
|---|---|---|---|
| Calcd.: | 61.81; | 5.49; | 6.36 |
| Found: | 61.61; | 5.41; | 6.34 |

EXAMPLE 8
Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid (2,4-dimethyl-3-pentyl) ester hydrochloride:

To dimethylformamide solution (1 ml) of the compound obtained in Example 7 (0.062 g, 0.1 mmol), N,N-dimethylaminopyridine (0.489 g, 4.00 mmol) and 2,4-dimethyl-3-pentanol (2 ml) was added dropwise, under ice-cooling (0° C.), phosphorus oxychloride (0.153 g, 1.0 mmol). The mixture was then heated for 12 hours under refluxing. The reaction mixture was partitioned between chloroform (200 ml) and water. The aqueous layer was subjected to extraction with chloroform (200 ml). The extract solutions were combined, washed with an aqueous sodium chloride solution and dried (Na$_2$SO$_4$), followed by distilling off the solvent under reduced pressure. The residue was purified by means of a silica gel column chromatography to give a colorless amorphous product (1.08 g, 82%). The product was dissolved in chloroform. To the solution was added a iON hydrogen chloride in ethanol to form a corresponding salt, which was recrystallized from chloroform-ether to give the titled compound as colorless crystalline powders. The structure of the compopund thus opbtained is shown in the below-mentioned Table 5.

m.p. 174–175° C.

Elemental Analysis for C$_{41}$H$_{45}$F$_2$N$_3$O$_4$S.HCl.H$_2$O:

|  | C (%) | H (%) | N (%) |
|---|---|---|---|
| Calcd.: | 64.09; | 6.30; | 5.47 |
| Found: | 64.31; | 6.13; | 5.48 |

EXAMPLE 9

Production of 4,7-dihydro-7-(2,6-difluorobenzyl)-3-(N-methyl-N-benzylaminomethyl)-2-(4-isobutyrylaminophenyl)-5-(tetrahydropyranylthio)carbonyl-4-oxo-thieno[2,3-b]pyridine hydrochloride:

In 2 ml of dichloromethane was dissolved 4-mercaptotetrahydrofuran (470 mg, 4.00 mmole), and to the solution was added dropwise a hexane solution (15 ml) of trimethyl aluminium (15%, 0.48 ml, 1.00 mmole) under ice-cooling. After one hour stirring at the same temperature, to the mixture dichloromethane solution (1 ml) of the compound (129 mg, 0.20 mmole) obtained in the above Reference Example 3 was added dropwise under ice-cooling. The reaction mixture was stirred for one hour, and then poured into 200 ml of distilled water. The resultant was subjected to extraction with chloroform, dried with a saturated aqueous solution of sodium chloride and dried (Na$_2$SO$_4$), followed by distilling off the solvent under reduced pressure. The residue thus obtained was subjected to a purification procedure of silica gel column chromatography to give a yellow amorphous product (30 mg, 11%). Thus obtained amorphous product was dissolved in chloroform, and to the solution was added 10N hydrogen chloride in ether to give a salt, and was recrystallized from chloroform-ether to give the titled compound as yellow crystals. The structure of the compound is shown in the below-mentioned Table 5.

m.p. 174–176° C.

Elemental Analysis for C$_{39}$H$_{39}$N$_5$O$_4$S$_2$F$_2$.HCl.2.5H$_2$O

C H N

Calcd.: 58.75; 5.69; 5.27 (%);

Found: 58.77; 5.59; 5.54 (%)

$^1$H-NMR(300 MHz, CDCl$_3$)δ: 1.28(6H,d,J=6.8 Hz), 1.75–1.87(2H,m), 1.97–2.04(2H,m), 2.11(3H,s), 2.56(1H, m), 3.54–3.61(2H,m), 3.66(2H,s), 3.87(1H,m), 3.96–4.01 (2H,m), 4.19(2H,s), 5.30(2H,m), 7.01(2H,dd,J=8.1 Hz), 7.12–7.32(5H,m), 7.42(1H,m), 7.62(2H,d,J=8.6 Hz), 7.80 (2H,d,J=8.6 Hz), 8.37(1H,s).

EXAMPLE 10

Employing the compound produced in Example 7 as the starting material, a procedure substantially the same as described in Example 9 was carried out to give compounds 10(1) and 10(2), whose structures are shown in the following Table 5.

TABLE 5

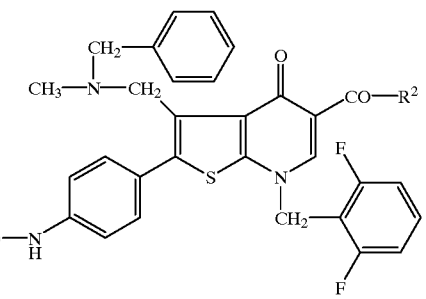

| Ex. No. | R$^2$ | yield (%) | m.p. (° C.) |
|---|---|---|---|
| 7 | hydroxy | 81 | 212–214 |
| 8 | 2,4-dimethyl-3-pentyloxy | 82 | 174–175 (hydrochloride) |
| 9 | 4-tetrahydropyranylthio | 11 | 174–176 (hydrochloride) |
| 10(1) | ethylthio | 53 | 251–253 (hydrochloride) |
| 10(2) | isopropylthio | 56 | 139–141 (hydrochloride) |

EXAMPLE 11

Production of 4,7-dihydro-7-(2,6-difluorobenzyl)-3-(N-methyl-N-benzylaminomethyl)-2-(4-isobutyrylaminophenyl)-6-methyl-4-oxo-thieno[2,3-b]pyridine-5-carboxylic acid isopropyl ester hydrochloride:

To an anhydrous tetrahydrofuran solution (50 ml) of the compound obtained in Example 5 (1.98 g, 2.78 mmole) was added dropwise a mixture of diethylether solution of methyl magnesium bromide (3.0M, 4.63 ml, 13.9 mmole) and copper iodide (529 mg, 2.78 mmole), under ice-cooling. The mixture was stirred for 0.5 hour at the same temperature, to the resultant was added 1N hydrogen chloride under ice-cooling to adjust to not more than pH 2, and then the mixture was stirred for 0.5 hour at room temperature. The reaction mixture was poured into a 500 ml aqueous solution of 0.1 N potassium hydroxide, the resultant was subjected to extraction with chloroform, dried with a saturated aqueous solution of sodium chloride and dried (Na$_2$SO$_4$), followed by distilling off the solvent under reduced pressure. The residue thus obtained was subjected to a purification procedure of silica gel column chromatography to give a yellow amorphous product (1.80 g, 96%).

To a tetrahydrofuran (15 ml) suspension of sodium hydride was added dropwise the tetrahydrofuran (15 ml) solution of the amorphous product (1.80 g, 2.67 mmole) obtained in the above at room temperature. After stirring the reaction mixture at 50° C. for 0.5 hour, a tetrahydrofuran (5 ml) solution of phenylselenyl chloride (1.02 g, 5.34 mmole) was added dropwise at 50° C. for one overnight. The. reaction mixture was poured into 500 ml of distilled water, extracted with chloroform, dried with a saturated sodium chloride and dried (Na$_2$SO$_4$), followed by distilling off the solvent under reduced pressure. The residue was subjected to a purification procedure of silica gel column chromatography to give a colorless amorphous product (1.00 g, 86%). Thus obtained amorphous product was dissolved in chloroform, and to the solution was added 10N hydrogen chloride in ether to give a salt, and was recrystallized from chloroform-ether to give the titled compound as white powdery crystals. The structure of the compound is shown in the below-mentioned Table 6.

m.p. 163–165° C.

Elemental Analysis for $C_{38}H_{39}N_3O_4SF_2 \cdot HCl \cdot 1.5H_2O$

|  | C | H | N |
|---|---|---|---|
| Calcd.: | 62.07; | 5.89; | 5.71 (%) |
| Found: | 62.31; | 5.81; | 6.04 (%) |

$^1$H-NMR(300 MHz, CDCl$_3$)δ: 1.23(6H, d, J=6.8 Hz), 1.38(6H, d, J=6.8 Hz), 2.10(3H, s), 2.45(3H, s), 2.54(1H, m), 3.63(2H, s), 4.13(2H, s), 5.30(1H, m), 5.34(3H, s), 6.93(2H, dd, J=8.1 Hz), 7.14–7.39(6H, m), 7.59(2H, d, J=8.6 Hz), 7.80(2H, d, J=8.6 Hz).

EXAMPLE 12

Employing the compound produced in Reference Example 3 as the starting material, Example 6(2), 6(3) or 6(4), a substantially the same procedure as described in Example 11 was conducted to give compounds 12(1), 12(2), 12(3) and 12(4), whose structures are shown in the below-mentioned Table 6.

EXAMPLE 13

Employing the compound produced in Reference Example 3 as the starting material, a substantially the same procedure as described in Example 11 was conducted using ethylmagnesium bromide instead of methylmagnesium bromide to give the compound 13, whose structure is shown in the below-mentioned Table 6.

EXAMPLE 14

Employing the compound produced in Example 4(1) or 4(22) as a starting material, a substantially the same procedure as described in Example 11 was conducted to give compounds 14(1) and 14(2), whose structures are shown in the following Table 6.

Employing the compound produced in Example 4(2), 4(3), 4(6), 4(7) or 4(8) as a starting material, a substantially the same procedure as described in Example 11 was conducted to give compounds 14(3) to 14(7), whose structures are shown in the following Table 6.

TABLE 6

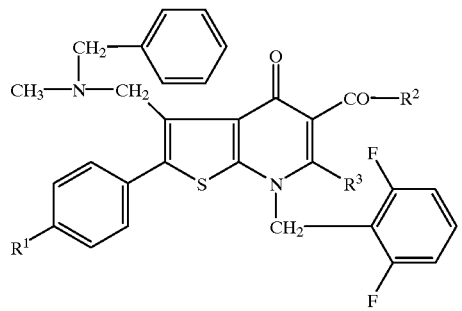

| Ex. No. | R$^1$ | R$^2$ | R$^3$ | yield (%) | m.p. (° C.) |
|---|---|---|---|---|---|
| 11 | isobutyryl-amino | isopropoxy | methyl | 76 | 163–165 (hydrochloride) |
| 12(1) | isobutyryl-amino | ethoxy | methyl | 32 | 179–181 (hydrochloride) |
| 12(2) | isobutyryl-amino | cyclohexyloxy | methyl | 18 | 158–160 (hydrochloride) |
| 12(3) | isobutyryl-amino | 3-pentyloxy | methyl | 35 | 157–159 (hydrochloride) |
| 12(4) | isobutyryl-amino | 4-tetrahydropyranyloxy | methyl | 34 | 170–172 (hydrochloride) |
| 13 | isobutyryl-amino | ethoxy | ethyl | 8 | 135–137 (hydrochloride) |
| 14(1) | allyloxy | isopropoxy | methyl | 79 | 143–145 (hydrochloride) |
| 14(2) | allyloxy | ethoxy | methyl | 95 | amorphous |
| 14(3) | 2-buten-1-yl-oxy | isopropoxy | methyl | | |
| 14(4) | allyloxy | cyclohexyloxy | methyl | | |
| 14(5) | cyclopropyl-methoxy | cyclohexyloxy | methyl | | |
| 14(6) | 2-buten-1-yl-oxy | cyclohexyloxy | methyl | | |
| 14(7) | cyclopropyl-methoxy | isopropoxy | methyl | | |

EXAMPLE 15

Using the compound produced in Example 3(1) or in Example 5 (100 mg), lactose (165 mg), corn starch (25 mg), polyvinyl alcohol (4 mg) and magnesium stearate (1 mg), tablets are prepared by a conventional method.

EXAMPLE 16

The compound produced in Example 3(1) or in Example 5 (5 g) is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

EXAMPLE 17

Using the compound produced in Example 3(4) (100 mg), crystalline cellulose (50 mg), low substituted hydroxypropylcellulose-31 (30 mg), hydroxypropylcellolose-L (6 mg) and magnesium stearate (1 mg), tablets are prepared by a conventional method.

EXAMPLE 18

Using the compound produced in Example 9 (100 mg), lactose (150 mg), cross carmelose sodium (30 mg), hydroxypropylcellulose (6 mg) and magnesium stearate (1 mg), tablets are prepared by a conventional method.

EXAMPLE 19

The compound produced in Example 11 (100 mg), lactose (165 mg), corn starch (25 mg), polyvinyl alcohol (4 mg) and magnesium stearate (1 mg), tablets are prepared by a conventional method.

EXAMPLE 20

Using the compound which is produced in Example 12(1) (100 mg), lactose (150 mg), low substituted hydroxypropylcellolose-31 (30 mg), polyvinylpyrrolidone (10 mg) and magnesium stearate (1 mg), tablets are prepared by a conventional method.

EXAMPLE 21

Using the compound which is produced in Example 14(1) or 14(2) (100 mg), lactose (150 mg), carboxymethylcellulose calcium (30 mg), hydroxypropylcellulose (6 mg) and magnesium stearate (1 mg), tablets are prepared by a conventional method.

EXAMPLE 22

| (1) | Compound produced in Example 3 (1) or in Example 5 | 5 g |
|---|---|---|
| (2) | Lactose.crystalline cellulose (granules) | 330 g |
| (3) | D-mannitol | 29 g |
| (4) | Low-substituted hydroxypropyl cellulose | 20 g |
| (5) | Talc | 25 g |
| (6) | Hydroxypropyl cellulose | 50 g |
| (7) | Aspartame | 3 g |
| (8) | Glycyrrhizic acid dipotassium salt | 3 g |
| (9) | Hydroxypropylmethyl cellulose 2910 | 30 g |
| (10) | Titanium oxide | 3.5 g |
| (11) | Yellow iron sesquioxide | 0.5 g |
| (12) | Light anhydrous silicic acid | 1 g |
| | Total | 500 g |

In pure water are suspended or dissolved (1), (3), (4), (5), (6), (7) and (8). The granule of (2) is coated with the suspension or solution to prepare raw fine granules, which are coated with (9) to (11) to prepare coated fine granules, which are mixed with (12), to give 500 g of fine granules containing 1% of the compound produced in Example 3(1) or Example 5. 500 mg each of thus-prepared fine granules is packed.

EXAMPLE 23

| (1) | Compound produced in Example 3 (4), 9, 11, 12 (1), 14 (1) or 14 (2) | 5 g |
|---|---|---|
| (2) | Lactose | 330 g |
| (3) | Corn starch | 150 g |
| (4) | Hydroxypropyl cellulose | 15 g |
| (5) | Light anhydrous silicic acid | 1 g |
| | Total | 500 g |

The above (1), (2) and (3) are mixed in a fluidized-bed granulating machine, and an aqueous solution of (4) is sprayed to the mixture in the granulating machine to give fine granules. After mixing with the (5), 500 mg each of thus prepared fine granules of the compound produced in Example 3(4), 9, 11, 12(1), 14(1) or 14(2) are packed.

EXPERIMENTAL EXAMPLE 1

(1) Preparation of $^{125}$I-leuprorelin:

Ten μl of $3\times10^{-4}$M aqueous solution of leuprorelin and 10 μl of 0.01 mg/ml lactoperoxidase in 0.1M HEPES buffer (pH 7.4) were taken into a tube, to which was added 10 μl (37 MBq in 0.1 M HEPES buffer (pH7.4)) of an Na$^{125}$I solution. The mixture was stirred, to which was added 10 μl of 0.001% H2O$_2$, then reaction was allowed to proceed for 20 minutes at room temperature. To the reaction mixture was added 700 μl of a 0.05% TFA solution to cease the reaction. The product was purified by means of reversed phase HPLC. Conditions of HPLC are as follows. $^{125}$I-leuprorelin was eluted at a retention time of 26 to 27 minutes.

| Column: | TSK gel ODS-80 ™CTR (4.6 mm x 10 cm) |
|---|---|
| Eluent: | Solvent A (0.05% TFA) |
| | Solvent B (40% CH$_3$CN-0.05% TFA) |
| | 0 minute (100% Solvent A) - 3 minutes (100% solvent A) - 7 minutes (50% solvent A + 50% solvent B) - 40 minutes (100% solvent B) |
| Elution temp.: | Room temperature |
| Flow rate: | 1 ml/min. |

(2) Preparation of membrane fraction of CHO (Chinese Hamster Ovary) cells containing human GnRH receptors CHO cells ($10^9$) expressing human GnRH receptors were suspended in a phosphate-buffered saline supplemented with 5 mM EDTA (ethylenediamine tetraacetate) (PBS-EDTA). The suspension was subjected to centrifugal separation for 5 minutes at 100×g. To the pellet of cells was added 10 ml of a homogenate buffer for cells (10 mM NaHCO$_3$, 5 mM EDTA, pH 7.5), which was homogenated by using a Polytron homogenizer. Centrifugal separation was conducted for 15 minutes at 400×g. The supernatant was taken into an ultracentrifugal tube, which was subjected to centrifuge for one hour at 100,000×g to give precipitate of the membrane fraction. The precipitates was suspended in 2 ml of the assay buffer (25 mM Tris-HCl, 1 mM EDTA, 0.1% BSA (bovine serum albumin), 0.25 mM PMSF, 1 μg/ml pepstatin, 20 μg/ml leupeptin, 100 μg/ml phosphoramide, 0.03% sodium azide, pH 7.5), which was centrifuged for one hour at 100,000×g. The membrane fraction recovered as precipitate was again suspended in 20 ml of the assay buffer, which was distributed to vials and stored at −80° C. until used.

(3) Determination of Inhibitory rate of $^{125}$I-leupororelin binding:

Membrane fraction of CHO cells expressing human GnRH receptors preparation in the above (2) as diluted with an assay buffer to 200 μg/ml and 188 μl each was distributed into tubes. 2 μl of 2 mM of the compound dissolved in 60% DMSO and 10 μl of 38 nM $^{125}$I-leuprorelin were added simultaneously to the CHO cell membrane fraction which expresses human GnRH receptors. For determining the amount of maximun binding, a solution for reaction supplemented with 2 μl of 60% DMSO and 10 μg of 38 nM $^{125}$I-leuprorelin was prepared. And, for determining the amount of non-specific binding, a solution for reaction supplemented with 2 μl of 100 μM leuprorelin dissolved in 60% DMSO and 10 μg of 38 nM $^{125}$I-leuprorelin were also prepared simultaneously.

The reaction was allowed to proceed at 25° C. for 60 minutes. The reaction mixture were respectively subjected to filtration under sucking with Whatman glass filter (GF-F) processed with polyethyleneimine. After completion of the filtration, radioactivity of the $^{125}$I-leuprorelin remaining on the filter paper was measured with a γ-counter.

By calculation of the following formula, the binding inhibitory rate (PMB, %) of each test compound was determined.

$$PMB=(TB-SB)/(TB-NSB)\times 100$$

TB: Maximum binding radioactivity.

SB: Radioactivity obtained when a compound was added.

NSB: Non-specific binding ratio activity.

Bisides, the inhibitory rates were determined by changing the concentrations of test compounds, and the concentration of a test compound inhibiting the (TB−NSB) by 50%, i.e. the concentration of PMB=50% ($IC_{50}$ value), was calculated by way of Hill plot.

The compound obtained in Example 3(4) was subjected to the above measurement methods, and obtained $IC_{50}$ value shown in the following Table 7.

TABLE 7

| $^{125}$I-leuprorelin binding inhibitory rate | |
|---|---|
| Test compound | $IC_{50}$ value (nM) Human GnRH receptor |
| Compound of Example 3 (4) | 10 |

INDUSTRIAL APPLICABILITY

A gonadotropin-releasing hormone antagonistic compound of the present invention has excellent properties on oral absorbing, stability, durability of actions and stability on metabolism. Therefore, the present compound can be used as a prophylactic or therapeutic agent for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agen t in both sexes (e.g. a pregnancy controlling agent and a menstrual cycle controlling agent); can be used as a contraceptive of male or female, as an ovulation-inducing agent of female; can be used as an infertility treating agent by using a rebound effect owing to a stoppage of administration thereof; is useful as modulating estrous cycles in animals in the field of animal husbandry, as an agent for improving the quality of edible meat or promoting the growth of animals; is useful as an agent of spawning promotion in fish.

We claim:
1. A compound of the formula:

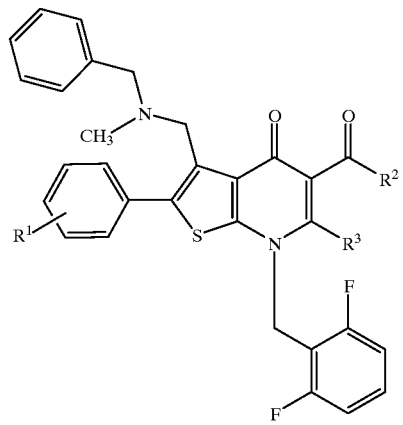

wherein $R^1$ is a $C_{1-8}$ alkanoylamino group;
$R^2$ is a group of the formula: —X—$R^{44}$ wherein X is O and $R^{44}$ is (i) a $C_{3-11}$ branched alkyl group which may optionally be substituted with $C_{1-4}$ alkyl, halogen, amino, mono- or di-$C_{1-4}$ alkylamino, $C_{1-4}$ alkoxy or $C_{3-7}$ cycloalkyl, or (ii) a 6-membered oxygen-containing heterocyclic group which may optionally be substituted with halogen, nitro, oxo, hydroxy, amino, mono- or di-$C_{1-4}$ alkylamino, $C_{1-4}$ alkoxy, $C_{1-4}$ alkyl or $C_{1-4}$ alkylthio; and
$R^3$ is a hydrogen atom or a alkyl group, or a salt thereof.

2. A compound according to claim 1, wherein $R^1$ is isobutyrylamino.

3. A compound according to claim 1, which is isopropyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; sec-butyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; 3-pentyl [4,7-dihydro-7-(2,6-difluorobenzyl)- 3-(N-benzyl-N-methylaminomethyl)-2-(4-isobutyrylaminophenyl)-4-oxothieno[2,3-b]pyridine-5-carboxylate]; tetrahydropyranyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; 2,4-dimethyl-3-pentyl [4,7-dihydro-7-(2,6-difluorobenzyl)-3-(N-benzyl-N-methylaminomethyl)-2-(4-isobutyrylaminophenyl)-4-oxothieno[2,3-b]pyridine-5-carboxylate]; isopropyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate]; 3-pentyl [4,7-dihydro-7-(2,6-difluorobenzyl)-3-(N-benzyl-N-methylaminomethyl)-2-(4-isobutyrylaminophenyl)-6-methyl-4-oxothieno[2,3-b]pyridine-5-carboxylate]; 4-tetrahydropyranyl [4,7-dihydro-7-(2,6-difluorobenzyl)-3-(N-benzyl-N-methylaminomethyl)-2-(4-isobutyrylaminophenyl)-6-methyl-4-oxothieno[2,3-b] pyridine-5-carboxylate], or a salt thereof.

4. A compound according to claim 1, which has a characteristic of high bioavailability when orally administered.

5. A compound according to claim 1, which is stable in plasma of blood.

6. A pharmaceutical/composition, which comprises a compound as defined in claim 1 and a carrier, excipient or diluent therefor.

7. A pharmaceutical composition according to claim 6, which is a composition for treating or preventing a sex hormone dependent disease.

8. A pharmaceutical composition according to claim 7, wherein the sex hormone dependent disease is prostatic cancer, uterus cancer, breast cancer or pituitary adenoma.

9. A pharmaceutical composition according to claim 8, wherein the sex hormone dependent disease is prostatauxe, endometriosis, myoma uteri or precocious puberty.

10. A pregnancy controlling composition, which comprises a compound or a salt thereof as defined in claim 1 and a carrier, excipient or diluent therefor.

11. A menstrual cycle controlling composition, which comprises a compound or a salt thereof as defined in claim 1 and a carrier, excipient or diluent therefor.

12. A composition according to claim 10, which is a composition for contraception.

13. A method for treating a mammal suffering from a gonadotropin-releasing hormone derived disorder, which comprises administering an effective amount of a compound as defined in claim 1 to the mammal.

14. A method for producing a compound of claim 1 or a salt thereof, which comprises (1) reacting a compound of the formula:

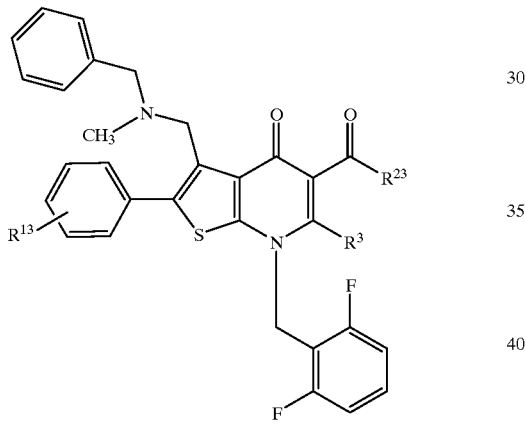

wherein $R^{13}$ is a $C_{1-8}$ alkanoylamino group, $R^{23}$ is a straight-chain alkoxy group, and $R^3$ is as defined in claim 1, with a compound of the formula:

$R^{44}$—H wherein $R^{44}$ is as defined in claim 1;

(2) reacting a compound of the formula:

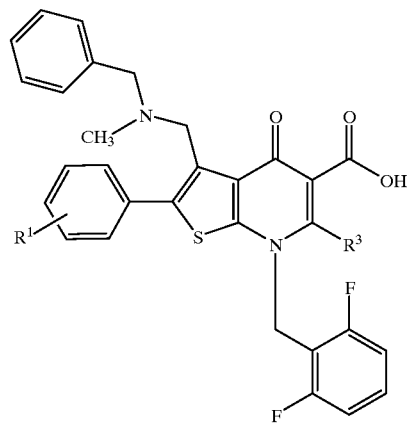

wherein each symbol is as defined in claim 1, with a compound of the formula:

$R^2$—H wherein $R^2$ is as defined in claim 1; or (3) reacting a compound of the formula:

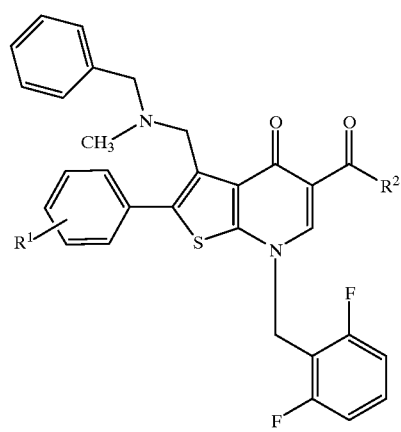

wherein each symbol is as defined in claim 1, with a compound of the formula:

$R^{32}$—Z wherein $R^{32}$ is an alkyl group and Z is an optionally halogenated metal, or its salt.

* * * * *